(12) United States Patent
Yun et al.

(10) Patent No.: US 9,850,500 B2
(45) Date of Patent: Dec. 26, 2017

(54) RECOMBINANT ADENOVIRUSES CAPABLE OF REGULATING ANGIOGENESIS

(76) Inventors: Chae-Ok Yun, Seoul (KR); Joo-Hang Kim, Seoul (KR); Jin Soo Kim, Seoul (KR); Hyun Chul Shin, Daejeon (KR); Yoon A Kang, Seoul (KR)

(*) Notice: Subject to any disclaimer, the term of this patent is extended or adjusted under 35 U.S.C. 154(b) by 1360 days.

(21) Appl. No.: 12/223,166

(22) PCT Filed: May 30, 2006

(86) PCT No.: PCT/KR2006/002083
§ 371 (c)(1),
(2), (4) Date: Jan. 13, 2010

(87) PCT Pub. No.: WO2007/086631
PCT Pub. Date: Aug. 2, 2007

(65) Prior Publication Data
US 2010/0215621 A1  Aug. 26, 2010

(30) Foreign Application Priority Data
Jan. 27, 2006  (KR) .................. 10-2006-0008981

(51) Int. Cl.
C12N 15/86 (2006.01)
A61K 48/00 (2006.01)

(52) U.S. Cl.
CPC ............ *C12N 15/86* (2013.01); *A61K 48/005* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 2003/0021776 A1* | 1/2003 | Rebar et al. | 424/94.63 |
| 2003/0104625 A1* | 6/2003 | Cheng et al. | 435/456 |
| 2005/0032186 A1* | 2/2005 | Kim et al. | 435/199 |
| 2006/0147420 A1* | 7/2006 | Fueyo | A61K 48/005 424/93.2 |

OTHER PUBLICATIONS

Isaac et al. (May 2002) *Homo sapiens* vascular endothelial growth factor (VEGF) gene, promoter region and partial cds. GenBank Accession No. AF095785, pp. 1-2 (direct submission by Isaac et al.).*
Li et al. (2005) Transcriptional targeting modalities in breast cancer gene therapy using adenovirus vectors controlled by alpha-lactalbumin promoter. Molecular Cancer Therapeutics 4(12): 1850-1859.*
Kang, et al., "Novel Cancer Antiangiotherapy Using the VEGF Promoter-Targeted Artificial Zinc-Finger Protein and Oncolytic Adenovirus", Molecular Therapy, Jun. 2008, vol. 16, No. 6, pp. 1033-1040.
Kang, et al., "Novel Cancer Antiangiotheraphy Using the VEGF Promoter-targeted Artificial Zinc-finger Protein and Oncolytic Adenovirus", Molecular Therapy, vol. 16, No. 6, pp. 1033-1040, Jun. 2008.

* cited by examiner

*Primary Examiner* — Addison D Ault
(74) *Attorney, Agent, or Firm* — Nath, Goldberg & Meyer; Joshua B. Goldberg; Tanya E. Harkins

(57) ABSTRACT

The present invention relates to a recombinant adenovirus capable of regulating angiogenesis, which comprises (a) an adenoviral UR (inverted terminal repeat) nucleotide sequence; and (b) a transcription regulatory sequence for a VEGF-A (vascular endothelial growth factor-A) gene comprising (i) a nucleotide sequence encoding a DNA binding domain comprising a zinc finger domain to bind to a site in a VEGF-A promoter sequence as set forth in nucleotides 1-2362 of SEQ ID NO:1, and (ii) a transcription activation domain or a transcription inhibitory domain linked to the nucleotide sequence encoding the DNA binding domain; and a pharmaceutical composition comprising the recombinant adenovirus.

3 Claims, 19 Drawing Sheets

Fig. 1a

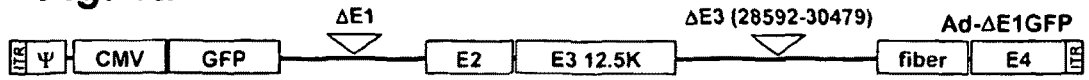

Fig. 1b

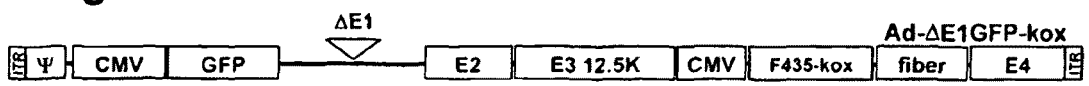

Fig. 1c

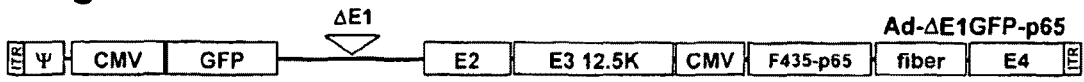

Fig. 1d

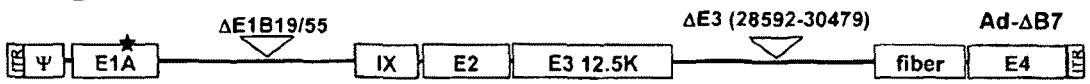

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1e

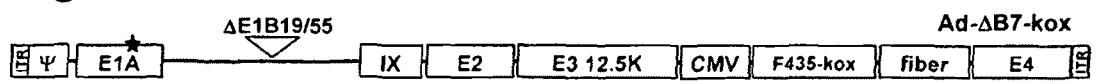

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1f

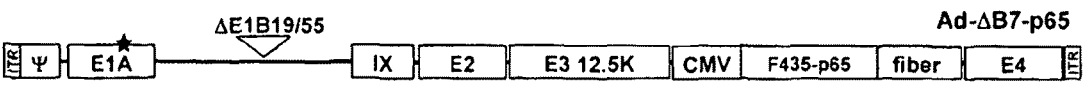

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1g

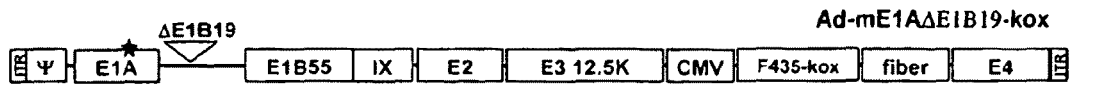

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1h

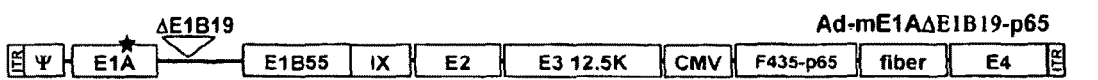

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1i

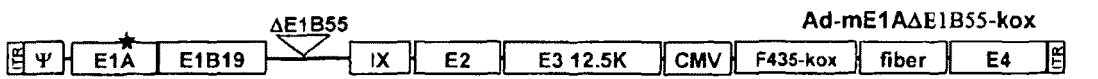

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1j

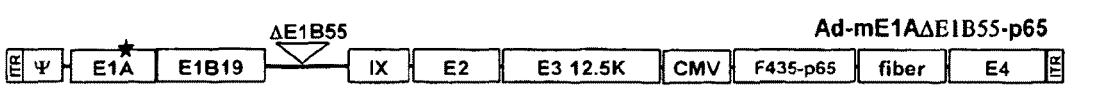

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).

Fig. 1q

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).
TSP denotes a tumor specific promoter.

Fig. 1r

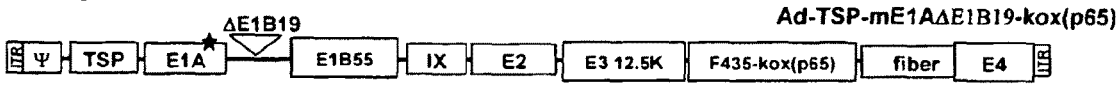

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).
TSP denotes a tumor specific promoter.

Fig. 1s

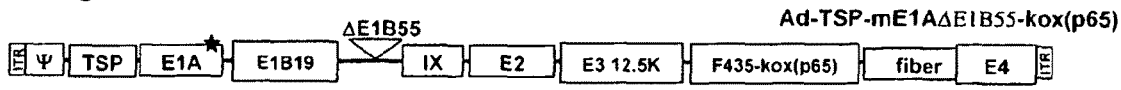

The asterisk symbol in the E1A region denotes mutated Rb binding sites in which a glutamic acid residue (Glu) positioned at amino acid 45 in CR1 is replaced by glycine(Gly) and 7 amino acid residues (DLTCHEA) in CR2 are replaced by 7 glycine residues (GGGGGGG).
TSP denotes a tumor specific promoter.

TSP denotes a tumor specific promoter.

TSP denotes a tumor specific promoter.

TSP denotes a tumor specific promoter.

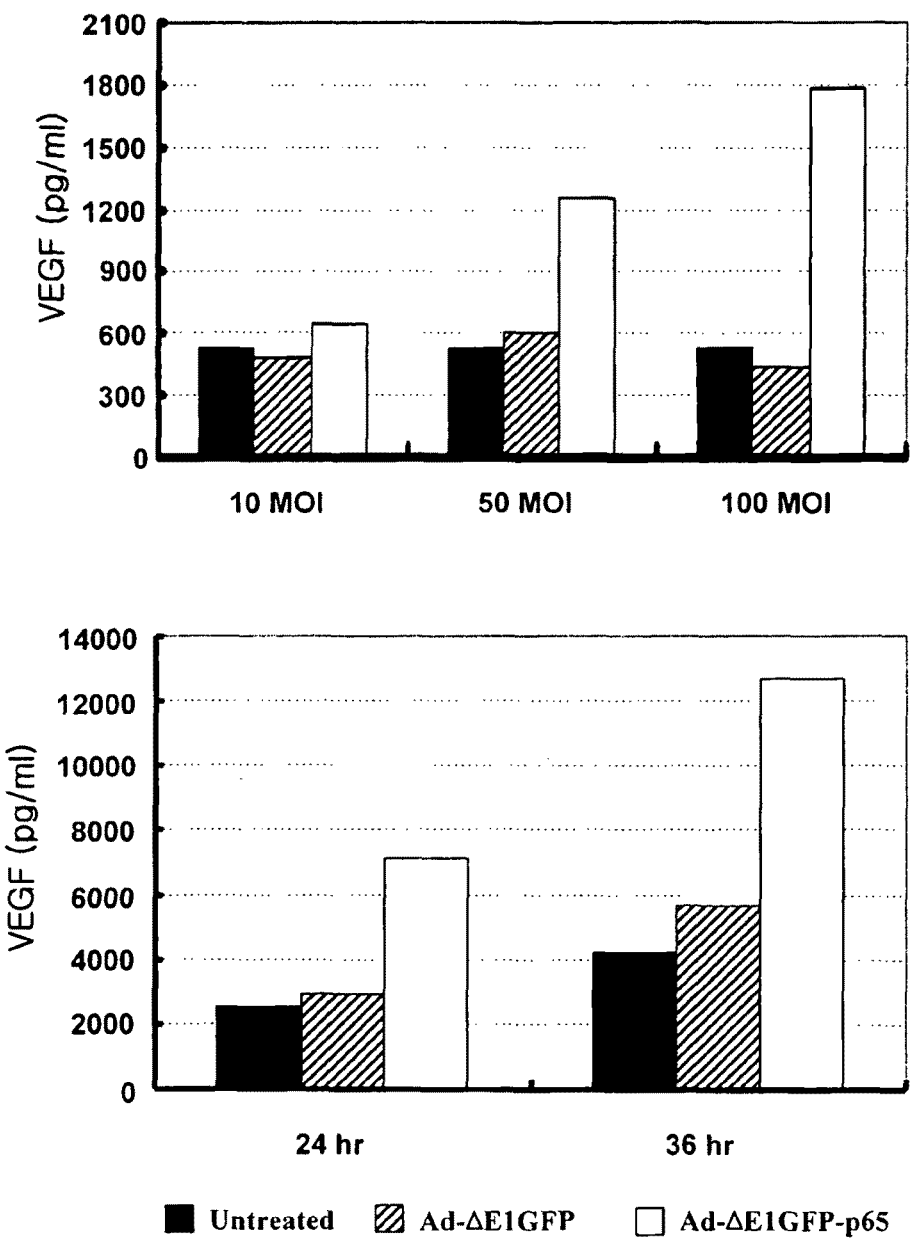

Fig. 4a
U343 X 40
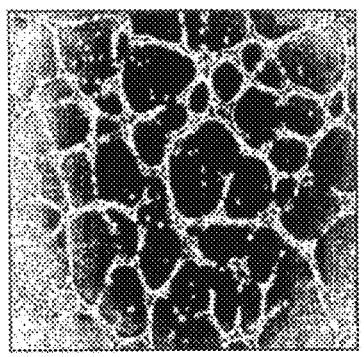 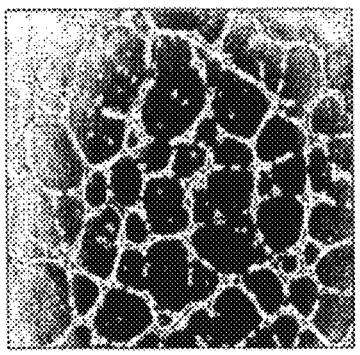 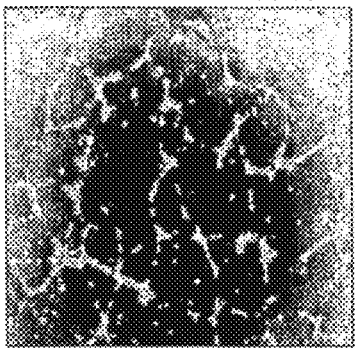
Untreated　　　　　　Ad-ΔE1GFP　　　　　Ad-ΔE1GFP-kox
U87MG X 40
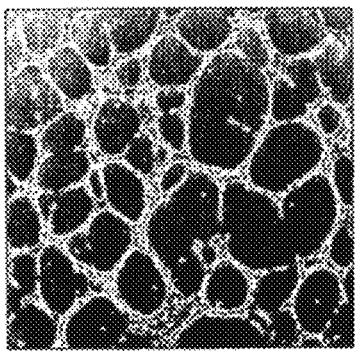 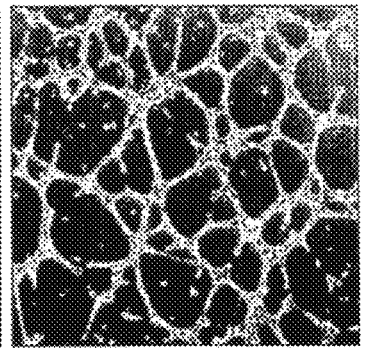 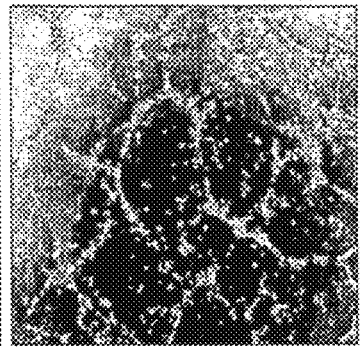
Untreated　　　　　　Ad-ΔE1GFP　　　　　Ad-ΔE1GFP-kox A1 : untreated
A2 : Ad-ΔE1GFP
A3 : Ad-ΔE1GFP-p65
A4 : VEGF (40 ng/ml)

E1 : untreated
E2 : Ad-ΔE1GFP
E3 : Ad-ΔE1GFP-p65
E4 : VEGF (40 ng/ml)

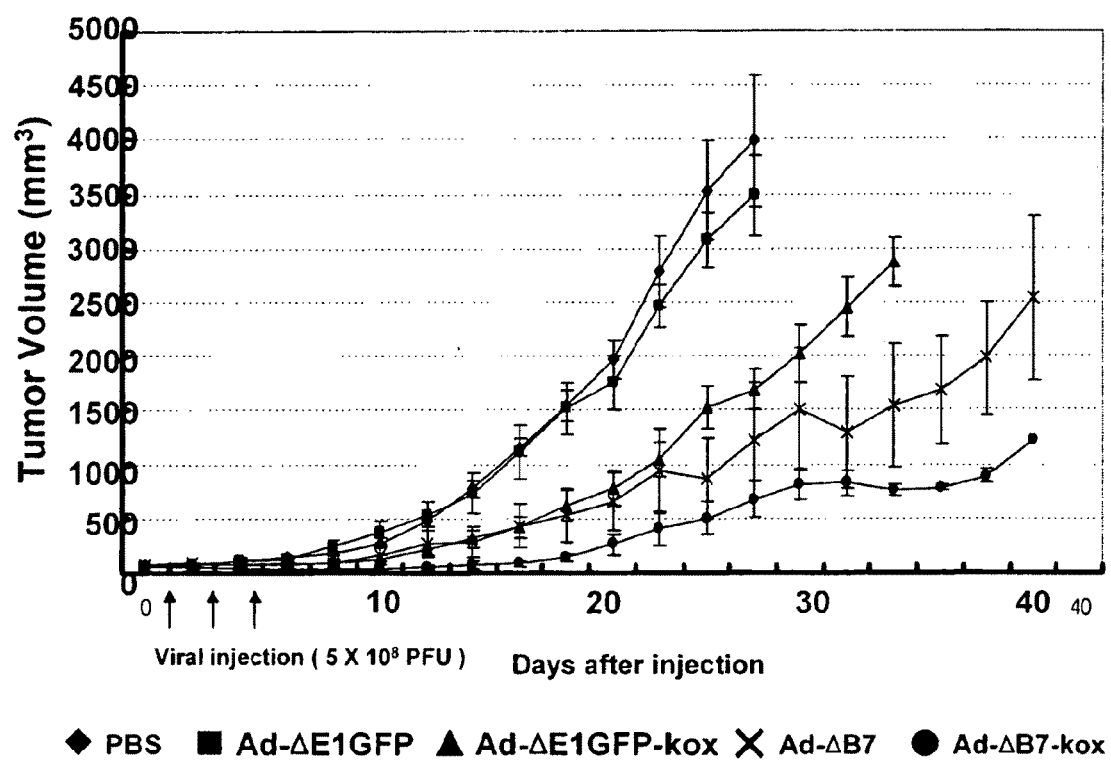

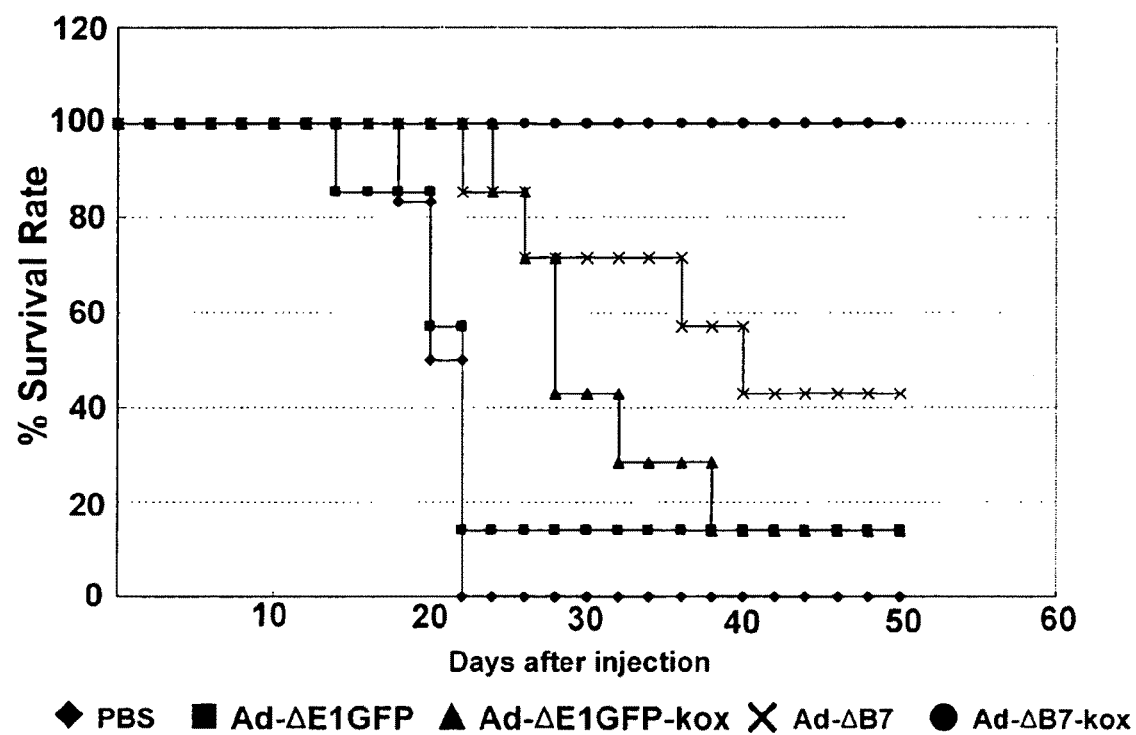

RECOMBINANT ADENOVIRUSES CAPABLE OF REGULATING ANGIOGENESIS

BACKGROUND OF THE INVENTION

Field of the Invention

The present invention relates to recombinant adenoviruses to regulate angiogenesis and pharmaceutical compositions for preventing or treating angiogenesis-related diseases.

Description of the Related Art

Vascular permeability factor (VPE) was first discovered by Senger group in the year of 1983[1] and the functions or actions of vascular endothelial growth factor (VEGF) were elucidated in 1989. Thereafter, VPE and VEGF were addressed as the same biomolecule and highlighted due to its critical role in angiogenesis of tumors.

VEGF-A is a potent inducer of angiogenesis and the lack of its single allele causes the inhibition of cardiovascular development to result in lethality in embryos[2], which demonstrates the requirement for the elaborate regulation of VEGF-A expression. To date, it has been reported that there are seven human VEGF-A isoforms ($VEGF_{121}$, $VEGF_{145}$, $VEGF_{148}$, $VEGF_{165}$, $VEGF_{183}$, $VEGF_{189}$ and $VEGF_{206}$), which are generated by alternative splicing of primary VEGF-A mRNA consisting of eight exons[3,4]. Recent research results suggest that VEGF is also involved in apoptosis inhibition, lymphangiogenesis, immune suppression and hematopoietic stem cell survival[5-8].

VEGE-mediated angiogenesis refers to successive processes to induce the growth of new capillary blood vessels from pre-existing blood vessels, and plays a critical role in tumor growth and invasion. VEGF-A is observed to be overexpressed in a variety of tumor cells[9]. Because a blood supply through angiogenesis is necessary in tumor growth, the inhibition of angiogenesis in tumor becomes an attractive target for anti-cancer therapy and some drugs such as angiostatin, endostatin, thrombospondin-1 and uPA-fragment have been developed as angiogenesis inhibitors[10]. The high expression of these angiogenesis inhibitors in tumor cells may be a potent therapeutic approach. It has been reported that some angiogenesis inhibitors such as angiostatin exhibit anti-cancer effects in a preclinical trial once they are administered[11].

However, angiogenesis inhibitors requires repeated administration due to their shorter half-life, causing serious problems such as toxicity, high cost and difficulty in determining suitable dosage. In contrast, gene therapy has plausible advantages such as high expression of angiogenesis inhibitors by single administration, cost effectiveness and introduction of at least one gene into body[12].

Adenoviruses are predominantly used as gene carriers for gene therapy for cancer, having some advantages including high gene transmission efficiency, feasible production at higher titer and convenient concentration. The single administration of replication incompetent adenoviruses expressing angiostatin has been suggested to inhibit the tumor growth by about 80% in U87MG glioma xenograft models[13]. In this regard, the high expression of anti-angiogenesis agents carried in adenoviruses would give rise to potent therapeutic effect on cancers.

Unlike anti-cancer therapy, therapeutic angiogenesis is a progressive approach aimed at increasing the number of collateral vessels delivering oxygen blood to ischemic tissue[14]. Conventional therapeutics including β-blockers, $Ca^{2+}$-antagonists, nitrates [coronary artery disease (CAD) treatment] and prostanoids [peripheral arterial occlusive disease (PAOD) treatment] promote no the growth of collateral vessels[10].

Growth factors are demanded to be expressed in initial phase for forming new blood vessels in ischemic tissues. The direct administration of recombinant growth factors is generally considered less inefficient than gene therapy. For example, the administration of VEGF and fibroblast growth factor (FGF) proteins to CAD patients has been shown to exhibit little or no therapeutic effects in clinical trials[16,17]. Unlikely, recombinant replication-incompetent adenoviruses expressing FGF-3 under the control of CMV (cytomegalo virus) promoter have been reported to be infected to about 25-30% cardiac muscles and induce the growth of new collateral vessels upon administering to coronary artery of pigs. In addition, the intracoronary gene-transfer using adenoviruses increases blood flow and contractile function in an ischemic region of the heart[18].

Because blood vessels are easily manipulated for gene transfer and short-term expression of transformed gene is enough to show therapeutic effects on ischemic diseases[19,20], an adenoviral gene therapy for ischemic diseases becomes promising. Where even a portion of cardiomyocytes or muscle cells is transformed with a therapeutic gene by gene therapy for ischemic diseases, they could express continuously growth factors for angiogenesis. In addition, since growth factors are required at an initial step for angiogenesis, therapeutic effects would be fully exhibited[10]. A local long-term expression of VEGF is likely to induce excessive angiogenesis and hemangioma[21]. The main targets of gene therapy for cardiovascular diseases include promotion of angiogenesis for coronary artery disease (CAD) and peripheral arterial occlusive disease (PAOD) and inhibition of postangioplasty stent restenosis[23,24].

To elevate the clinical applicability of gene therapy, it is critical to provide a system for specifically regulating the expression of therapeutic genes. The transcription of a gene is regulated in vivo by transcription factors composed of two functional domains. Of them, a DNA binding domain recognizes and binds to a specific DNA sequence and a regulation domain controls transcription of a gene[25]. $Cys_2$-$His_2$ zinc finger proteins form the largest family of eukaryotic transcription factors and comprise more than half of transcription factors present in a human genome[26]. In this regard, zinc finger proteins could provide a pivotal structural platform for preparing artificial transcription factors[27].

Zinc finger domains capable of binding to a specific DNA sequence are linked to natural-occurring transcription activation domain or repression domain to provide artificial transcription factors that could recognize target genes and promote or repress their expression. This approach permits to regulate gene expression with no modification of target DNA sequences. Several reports describe that artificial zinc finger proteins could successfully regulate endogenous chromosomal genes[28-30].

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel recombinant adenoviruses to effectively regulate angiogenesis in human, in particular, recombinant adenoviruses to repress angiogenesis for elevating anti-tumor effects, and recombinant adenoviruses to promote angiogenesis to supply oxygen and nutrient molecules to the heart and ischemic tissues in extremities for preventing necrosis and restoring normal physiological functions. As a result, the present inventors have constructed novel recombinant adenoviruses carrying artificial transcription factors to effectively regulate the expression of the human VEGF-A (vascular endothelial growth factor-A) gene and have discovered that the recombinant adenoviruses excellently regulated angiogenesis.

Accordingly, it is an object of this invention to provide a recombinant adenovirus capable of regulating angiogenesis.

It is another object of this invention to provide a pharmaceutical composition or method for preventing or treating an angiogenesis-associated disease.

Other objects and advantages of the present invention will become apparent from the detailed description to follow and together with the appended claims and drawings.

DETAILED DESCRIPTION OF THIS INVENTION

In one aspect of this invention, there is provided a recombinant adenovirus capable of regulating angiogenesis, comprising: (a) an adenoviral ITR (inverted terminal repeat) nucleotide sequence; and (b) a transcription regulatory sequence for a VEGF-A (vascular endothelial growth factor-A) gene comprising (i) a nucleotide sequence encoding a DNA binding domain comprising a zinc finger domain to bind to a site in a VEGF-A promoter sequence as set forth in nucleotides 1-2362 of SEQ ID NO:1, and (ii) a transcription activation domain or a transcription inhibitory domain linked to the nucleotide sequence encoding the DNA binding domain.

The present inventors have made intensive researches to develop novel recombinant adenoviruses to effectively regulate angiogenesis in human, in particular, recombinant adenoviruses to repress angiogenesis for elevating anti-tumor effects, and recombinant adenoviruses to promote angiogenesis to supply oxygen and nutrient molecules to the heart and ischemic tissues for preventing necrosis and restoring normal physiological functions. As a result, the present inventors have constructed novel recombinant adenoviruses carrying artificial transcription factors to effectively regulate the expression of the human VEGF-A (vascular endothelial growth factor-A) gene and have discovered that the recombinant adenoviruses excellently regulated angiogenesis. In addition, the present inventors have discovered the most superior partner for artificial transcription, i.e., a pair consisting of DNA binding domain and effector.

Transcription factors are generally composed of two type domains each of which exhibits distinctly different function. One of them is a DNA biding domain specifically recognizing a DNA sequence and the other is an effector (i.e., transcription activation domain or transcription inhibitory domain) to promote or inhibit transcription by interacting other proteins. The reason why transcription factors act on a specific gene among a multitude of genes is that they have a distinctly different DNA binding domain. DNA binding domains recognize and bind to a specific nucleotide sequence of a gene, which permits transcription factors to act on transcription of only the gene. The two type domains are modular in structure and function. Therefore, where DNA binding domains can be artificially constructed, they would be linked to transcription activation domains or transcription inhibitory domains to provide tailor-made transcription factors for selectively regulating the expression of a gene.

One of strategies of this invention is to prepare artificial transcription factors containing zinc finger domains that have much higher potential to regulate the expression of VEGF-A than antisense oligonucleotides and RNA-interference. More specifically, for maintaining the transcription repression activity, both antisense and RNA-interference approaches are required to bind to several copies of mRNA in a cell; however, artificial transcription factors are required to bind to only each allele of a VEGF-A gene locus. In this regard, artificial transcription factors play their inherent roles irrespective of the expression level of the VEGF-A gene. In addition, since artificial transcription factors allow for the expression of all isoforms of VEGF-A, they are beneficial in promoting angiogenesis.

Zinc finger domains are small polypeptide domains of approximately 30 amino acid residues in which there are four residues, either cysteine or histidine, appropriately spaced such that they can coordinate a zinc ion (Klug and Rhodes, *Trends Biochem. Sci.* 12:464-469 (1987); Evans and Hollenberg, *Cell* 52:1-3 (1988); Payre and Vincent, *FEBS Lett.* 234:245-250 (1988); Miller et al., *EMBO J.* 4:1609-1614 (1985); Berg, *Proc. Natl. Acad. Sci. U.S.A.* 85:99-102 (1988); and Rosenfeld and Margalit, *J. Biomol. Struct. Dyn,* 11: 557-570 (1993)). Zinc finger domains can be categorized according to the identity of the residues that coordinate the zinc ion, e.g., as the $Cys_2$-$His_2$ class, the $Cys_2$-$Cys_2$ class, the $Cys_2$-CysHis class and so forth. In the present invention, the $Cys_t$-$His_t$ class is the most preferable. The zinc coordinating residues of $Cys_2$-$His_2$ zinc fingers are typically spaced as follows:

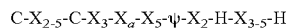

wherein amino acids are represented by one-letter symbol, ψ is a hydrophobic residue (Wolfe et al., *Annu. Rev. Biophys. Biomol. Struct.* 3:183-212 (1999)), X represents any amino acid, the subscript number indicates the number of amino acids, and a subscript with two hyphenated numbers indicates a typical range of intervening amino acids, and $X_a$ represents phenylalanine(F) or tyrosine(Y).

For convenience, the main DNA contacting residues of a zinc finger domain are numbered: −1, 2, 3, and 6 based on the following example: The numbers are allocated with reference to a alpha helix structure in the tertiary structure of zinc finger domains. In the following example, X located in R-X-D sequence is allocated as number 1.

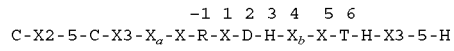

($X_a$ represents phenylalanine(F) or tyrosine(Y), and $X_b$ represents amino acid residues having hydrophobic R-groups)

As noted in the example above, the DNA contacting residues are Arg (R), Asp (D), His (H), and Thr (T). The above motif can be abbreviated RDHT. The following Table summarizes exemplary zinc finger domains useful in constructing DNA binding domains. It is obvious to one of skill in the art that other zinc finger domains also can be utilized for preparing DNA binding domains.

TABLE 1

| Name of zinc finger domain | Amino acid sequence | SEQ ID NO |
|---|---|---|
| CSNR | YKCKQCGKAFGCPSNLRRHGRTH | 13 |
| DSAR | YSCGICGKSFSDSSAKRRHCILH | 14 |
| DSCR | YTCSDCGKAFRDKSCLNRHRRTH | 15 |
| QSHR | YKCGQCGKFYSQVSHLTRHQKIH | 16 |
| QSHT | YKCEECGKAFRQSSHLTTHKIIH | 17 |
| QSNR | YECEKCGKAFNQSSNLTRHKKSH | 18 |
| QSNV | YVCSKCGKAFTQSSNLTVHQKIH | 19 |
| QSSR | YKCPDCGKSFSQSSSLIRHQRTH | 20 |
| RDER | YVCDVEGCTWKFARSDELNRHKKRH | 21 |
| RDHT | FQCKTCQRKFSRSDHLKTHTRTH | 22 |
| RSHR | YKCMECGKAFNRRSHLTRHQRIH | 23 |
| RSNR | YICRKCGRGFSRKSNLIRHQRTH | 24 |
| VSNV | YECDHCGKAFSVSSNLNVHRRIH | 25 |
| VSSR | YTCKQCGKAFSVSSSLRRHETTH | 26 |
| VSTR | YECNYCGKTFSVSSTLIRHQRIH | 27 |
| WSNR | YRCEECGKAFRWPSNLTRHKRIH | 28 |
| QSHV | YECDHCGKSFSQSSHLNVHKRTH | 29 |
| RDHR | FLCQYCAQRFGRKDHLTRHMKKS | 30 |
| DSNR | YRCKYCDRSFSDSSNLQRHVRNIH | 31 |
| QTHR | YECHDCGKSFRQSTHLTRHRRIH | 32 |

Preferably, the DNA binding domain used in this invention comprises a plurality of zinc finger domains, more preferably 2-6, still more preferably 2-4, most preferably 3-4 zinc finger domains.

The zinc finger domains used in this invention bind to a site in a VEGF-A (vascular endothelial growth factor-A) promoter sequence as set forth in nucleotides 1-2362 of SEQ ID NO:1.

According to a preferred embodiment, the zinc finger domain of the DNA binding domain comprises the amino acid sequence selected from the group consisting of amino acid sequences of SEQ ID NOs:13-32.

More preferably, the DNA binding domain comprises, in N-terminal to C-terminal order, first, second and third zinc finger domains, wherein
  (1) DNA contacting residues at positions −1, 2, 3, and 6 of the first zinc finger domain are QSHR, those of the second zinc finger domain are RDHT, and those of the third zinc finger domain are RSHR; (e.g., SEQ ID NO:2)
  (2) DNA contacting residues at positions −1, 2, 3, and 6 of the first zinc finger domain are QSHR, those of the second zinc finger domain are RDHT, and those of the third zinc finger domain are RSNR; (e.g., SEQ ID NO:3)
  (3) DNA contacting residues at positions −1, 2, 3, and 6 of the first zinc finger domain are RSHR, those of the second zinc finger domain are RDHT, and those of the third zinc finger domain are RSHR; (e.g., SEQ ID NO:4)
  (4) DNA contacting residues at positions −1, 2, 3, and 6 of the first zinc finger domain are QSHT, those of the second zinc finger domain are DSAR, and those of the third zinc finger domain are RSNR; (e.g., SEQ ID NO:5) or
  (5) DNA contacting residues at positions −1, 2, 3, and 6 of the first zinc finger domain are QTHR, those of the second zinc finger domain are RDHT, and those of the third zinc finger domain are RSHR (e.g., SEQ ID NO:6).

According to a preferred embodiment, the nucleotide sequence encoding the DNA binding domain comprising a plurality of the zinc finger domains codes for the amino acid sequence selected from the group consisting of SEQ ID NOs:2-5 and 12. More preferably, the nucleotide sequence encoding the DNA binding domain comprising a plurality of the zinc finger domains codes for the amino acid sequence of SEQ ID NO:2 or 11, most preferably SEQ ID NO:2. The most preferable nucleotide sequences encoding the DNA binding domain of SEQ ID NO:2 or 11 are set forth in SEQ ID NOs: 8 and 11, respectively.

According to a preferred embodiment, the transcription activation domain linked to the DNA binding domain is Gal4 activation domain, VP16 domain derived from herpes simplex virus or p65 domain of NF-κB, most preferably p65 domain. The exemplary amino acid sequence of p65 domain is indicated in SEQ ID NO:6. The most preferable nucleotide sequence encoding p65 domain is indicated in SEQ ID NO:9.

According to a preferred embodiment, the transcription inhibitory domain linked to the DNA binding domain is that originated from Kox 1, Kid (Witzgall R. et al. *Proc. Natl. Acad. Sci. U.S.A.*, 91(10):4514-8 (1994)), UME6, ORANGE, groucho or WRPW (Dawson et. al., *Mol. Cell Biol.* 15:6923-31 (1995)) proteins. Most preferably, the transcription inhibitory domain is KOX inhibitory domain originated from the Kox 1 protein. A first exemplary inhibitory domain is the KRAB domain from the Kid protein. A second exemplary inhibitory domain is the KOX inhibitory domain. This domain includes the KRAB domain from the human Kox1 protein (see SEQ ID NO:7). The most preferable nucleotide sequence encoding the KOX domain is set forth in SEQ ID NO:10.

According to a preferred embodiment, the transcription regulatory sequence for the VEGF-A gene is in the fusion form composed of the DNA binding domain of any one of SEQ ID NOs:2-5 linked to the p65 domain or KOX domain. More preferably, the transcription regulatory sequence for the VEGF-A gene is in the fusion form composed of the DNA binding domain of SEQ ID NO:2 linked to the p65 domain or KOX domain.

The DNA binding domain may be directly or indirectly linked to the transcription activation domain or transcription inhibitory domain, preferably indirectly linked to the transcription activation domain or transcription inhibitory domain through linkers. For example, two domains are linked to each other through linker such as Ala-Ala-Ala-Lys-Phe or (Ala)$_3$.

The nucleotide sequence coding for DNA binding domain-transcription activation (inhibitory) domain, i.e., the sequence for regulating the expression of the VEGF-A gene is incorporated into adenoviral genome sequences. It is preferred that the sequence for regulating the expression of the VEGF-A gene is present in a suitable expression construct. According the expression construct, it is preferred that the transcription regulatory sequence for the VEGF-A gene is operatively linked to a promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. According to the present invention, the promoter linked to the transcription regulatory sequence is operable in, preferably, animal, more preferably, mammalian cells, to control transcription of the transcription regulatory sequence, including the promoters derived from the genome of mammalian cells or from mammalian viruses, for example, U6 promoter, H1 promoter, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, inducible promoter, tumor specific promoter (e.g., TERT promoter, PSA promoter, PSMA promoter, CEA promoter, E2F promoter and AFP promoter) and tissue specific promoter (e.g., albumin promoter). Most preferably, the promoter is CMV promoter or tumor specific promoter. Where the tumor specific promoter is used, TERT promoter or E2F promoter is preferable. As TERT (telomerase reverse transcriptase) promoter, wild type human hTERT (human telomerase reverse transcriptase) promoter or m-hTERT developed by this inventors (see Korean Pat. No. 523028) may be used. mTERT is constructed in such a manner that at least one (preferably, one) additional c-Myc binding site and at least one (preferably, five) additional Sp1 binding site are linked to human telomere reverse transcriptase promoter comprising two c-Myc binding sites and five Sp1 binding sites. The exemplary nucleotide sequence of m-hTERT is set forth in SEQ ID NO:33. The E2F promoter is derived from the E2F gene involving in cell cycle (Johnson, D. G., *Mol. Carcinog.* 27: 151-157 (2000); Ngwenya, S., and Safe, S., *Endocrinology* 144:1675-1685; Cam, H., and Dynlacht, D., *Cancer Cell* 3:311-316 (2003)), exemplary sequence of which is described in SEQ ID NO:34.

Cancer gene therapy using adenoviruses has been highlighted because the expression of therapeutic genes is not required to maintain over the life span of patients and immune responses to adenoviruses are not problematic. Therefore, the present invention utilizes adenoviral genome backbones for cancer gene therapy.

Adenovirus has been usually employed as a gene delivery system because of its mid-sized genome, ease of manipulation, high titer, wide target-cell range, and high infectivity. Both ends of the viral genome contains 100-200 by ITRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

A small portion of adenoviral genome is known to be necessary as cis elements (Tooza, *J. Molecular biology of DNA Tumor viruses,* 2nd ed. Cold Spring Harbor Laboratory, Cold Spring Harbor, N.Y. (1981)), allowing substitution of large pieces of adenoviral DNA with foreign sequences, particularly together with the use of suitable cell lines such as 293. In this context, the recombinant adenovirus comprises the adenoviral ITR sequence as an essential sequence as well as the transcription regulatory sequence for the VEGF-A gene.

It is preferred that the transcription regulatory sequence for the VEGF-A gene is inserted into either the deleted E1 region (E1A region and/or E1B region, preferably, E1B region) or the deleted E3 region, more preferably, the deleted E3 region. Another foreign sequence (e.g., cytokine genes, immuno-costimulatory factor genes, apoptotic genes and tumor suppressor genes) is additionally inserted into the recombinant adenovirus, preferably into either the deleted E1 region (E1A region and/or E1B region, preferably, E1B region) or the deleted E3 region, more preferably, the deleted E1 region (E1A region and/or E1B region, most preferably, E1B region). Furthermore, the inserted sequences may be incorporated into the deleted E4 region.

In nature, adenovirus can package approximately 105% of the wild-type genome, providing capacity for about extra 2 kb of DNA. In this regard, the foreign sequences described above inserted into adenovirus may be further inserted into adenoviral wild-type genome.

According to a preferred embodiment, the recombinant adenovirus of this invention comprises the inactivated E1B 19 gene, inactivated E1B 55 gene or inactivated E1B 19/E1B 55 gene. The term "inactivation" in conjunction with genes used herein refers to conditions to render transcription and/or translation of genes to occur non-functionally, thereby the correct function of proteins encoded genes cannot be elicited. For example, the inactivated E1B 19 gene is a gene incapable of producing the functional E1B 19 kDa protein by mutation (substitution, addition, and partial and whole deletion). The defect E1B 19 gives rise to the increase in apoptotic incidence and the defect E1B 55 makes a recombinant adenovirus tumor-specific (see Korean Pat. Appln. No. 2002-23760). The term used herein "deletion" with reference to viral genome encompasses whole deletion and partial deletion as well.

According to a preferred embodiment, where the recombinant adenovirus comprises the transcription activation domain, it is preferred that the recombinant adenovirus comprises an inactive E1A gene; in the case that the recombinant adenovirus comprises the transcription activation domain, it is preferred that the recombinant adenovirus comprises an active E1A gene. The recombinant adenovirus carrying the active E1A gene is replication competent. According to a more preferred embodiment, the recombinant adenovirus comprises the inactive E1B 19 gene and active E1A gene. Still more preferably, the recombinant adenovirus of this invention comprises the inactive E1B 19 gene and active E1A gene, and the transcription regulatory sequence for the VEGF-A gene in a deleted E3 region (e.g., FIGS. 1*m*, 1*n* and 1*u*).

According to the most preferred embodiment, the recombinant adenovirus of this invention comprises the inactive E1B gene and mutated active E1A gene, and the transcription regulatory sequence for the VEGF-A gene in a deleted E3 region (e.g., FIGS. 1*e*, 1*f* and 1*q*). The mutated active E1A gene refers to E1A region having a mutated Rb (retinoblastoma protein) binding region in which a Glu residue positioned at amino acid 45 of the Rb-binding region is substituted with a Gly residue and all of amino acids positioned at amino acids 121-127 of the Rb-binding region are substituted with Gly residues.

It has been already suggested that tumor cells have mutated Rb and impaired Rb-related signal pathway as well as mutated p53 protein. Hence, the replication of adenoviruses lacking Rb binding capacity is suppressed in normal cells by virtue of Rb activity, whereas adenoviruses lacking Rb binding capacity actively replicate in tumor cells with repressed Rb activity to selectively kill tumor cells[31,32]. In this context, the recombinant adenoviruses with the mutated Rb binding region show significant tumor specific oncolytic activity.

Alternatively, the recombinant adenoviruses of this invention comprise a tumor specific promoter operatively linked to the active E1A gene to elevate cancer cell selectivity of E1A gene expression, permitting viruses to be propagated in more tumor-specific manner. Where the tumor specific promoter is used, TERT promoter or E2F promoter is preferable. More preferably, TERT promoter is used as tumor specific promoters, most preferably, m-hTERT developed by the inventors. The exemplary adenoviruses carrying tumor specific promoter (TSP) are represented in FIGS. 1q-1v.

According to a preferred embodiment, the recombinant adenovirus has a genetic map selected from the group consisting of FIGS. 1e-1v. More preferably, the recombinant adenovirus of this invention is represented by FIGS. 1e-1h, 1k-1n, 1q-1r and 1t-1u, most preferably, FIGS. 1e, 1f and 1q.

As demonstrated in Examples described hereunder, the recombinant adenovirus of this invention capable of regulating the expression of the VEGF-A gene represses or promotes the expression of all isoforms of VEGF-A and provides promising therapeutics to prevent or treat angiogenesis-associated diseases. In particular, the recombinant adenoviruses carrying transcription inhibitory domains selectively suppress angiogenesis in tumor to dramatically elevate anti-tumor effects. Furthermore, the recombinant adenoviruses carrying transcription inhibitory domains can induce tumor cell-killing effects even at lower titers, contributing to significant safety in human application.

In another aspect of this invention, there is provided a pharmaceutical composition for preventing or treating an angiogenesis-associated disease, which comprises (a) a therapeutically effective amount of the recombinant adenovirus capable of regulating angiogenesis described hereinabove; and (b) a pharmaceutically acceptable carrier.

In still another aspect of this invention, there is provided a method for preventing or treating an angiogenesis-associated disease, comprising administering to a patient a pharmaceutical composition comprising a therapeutically effective amount of the recombinant adenovirus capable of regulating angiogenesis described above.

Since the recombinant adenovirus contained as active ingredients in the pharmaceutical composition is identical to the angiogenesis-regulating recombinant adenovirus of this invention described above, the detailed descriptions of the recombinant adenovirus indicated above are common to the pharmaceutical composition. Therefore, the common descriptions between them are omitted in order, to avoid undue redundancy leading to the complexity of this specification.

The recombinant adenoviruses expressing VEGF-A-specific artificial transcription factors effectively inhibit or promote angiogenesis to be very useful in treating angiogenesis-associated diseases, in particular, exhibiting significantly increased anti-tumor effects. Where the recombinant adenoviruses comprise the inactivated E1B 55 gene or mutated Rb binding sites in E1A region, they show excellent tumor-specificity. These features and advantages allow to decrease effective dosage of viruses for treating cancer and reduce toxicity and immune responses associated with virus administration.

According to a preferred embodiment, the recombinant adenovirus comprises the transcription activation domain in the transcription regulatory sequence for the VEGF-A gene and the angiogenesis-associated disease is ischemic cardiovascular disease, e.g., coronary artery disease (CAD) and peripheral arterial occlusive disease (PAOD).

According to a preferred embodiment, the recombinant adenovirus comprises the transcription inhibitory domain in the transcription regulatory sequence for the VEGF-A gene and the angiogenesis-associated disease is rheumatoid arthritis, diabetic retinopathy, cancer, hemangioma or psoriasis, most preferably, cancer.

Since the recombinant adenovirus contained the pharmaceutical composition has oncolytic effect to a wide variety of tumor cells, the pharmaceutical composition of this invention is useful in treating tumor-related diseases, including stomach cancer, lung cancer, breast cancer, ovarian cancer, liver cancer, bronchogenic cancer, nasopharyngeal cancer, laryngeal cancer, pancreatic cancer, bladder cancer, colon cancer, and uterine cervical cancer.

The term "prevention" as used herein refers to inhibition of the occurrence of disease or disorder in animals susceptible to the disease or disorder. The term "treatment" as used herein, refers to (a) suppression of disease or disorder development; (b) alleviation of disease or disorder; and (c) curing of disease or disorder. Therefore, the term "therapeutically effective amount" as used herein means an amount sufficient to achieve the pharmaceutical effect described above.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative.

The pharmaceutical composition according to the present invention may be preferably administered parenterally, i.e., by intravenous, intraperitoneal, intratumoral, intramuscular, subcutaneous, intracardiomuscular or local administration. For example, the pharmaceutical composition may be administered intraperitoneally to treat ovarian cancer and intravenously to treat liver cancer, directly injected to visible tumor mass to treat breast cancer, directly injected to enema to treat colon cancer, and directly injected to a catheter to treat bladder cancer.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, the pharmaceutical composition of the present invention comprises $1\times10^5$-$1\times10^{15}$ pfu/ml of a recombinant adenovirus, and $1\times10^{10}$ pfu of a recombinant adenovirus is typically injected once every other day over two weeks.

According to the conventional techniques known to those skilled in the art, the pharmaceutical composition comprising the recombinant adenovirus according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition comprising the recombinant adenovirus according to the present invention may be utilized alone or in combination with typical chemotherapy or radiotherapy. Such combination therapy may be more effective in treating cancer. The chemotherapeutic agents useful for the combination therapy include cisplatin, carboplatin, procarbazine, mechlorethamine, cyclophosphamide, ifosfamide, melphalan, chlorambucil, bisulfan, nikosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

BRIEF DESCRIPTION OF THE DRAWINGS

FIGS. 1a-1v schematically represent genetic maps of adenoviral vectors used in Examples. All indicated adenoviral vectors were derived from full-length adenovirus genomes cloned and manipulated in *E. coli* as bacterial plasmids. In FIGS. 1a-1c, Ad-ΔE1GFP has the whole E1 region deleted and expresses GFP (green fluorescence protein) gene under the control of CMV promoter inserted into the E1 region. Ad-ΔE1GFP-kox and Ad-ΔE1GFP-p65 have F435-kox and F435-p65 in E3 region, respectively. In FIGS. 1d-1p, Ad-ΔB7 contains mutated E1A, but lacks E1B 19 kDa and E1B 55 kDa. The symbol "★" denotes mutated Rb (retinoblastoma) binding sites in E1A ions in which a glutamic acid residue (Glu) positioned at amino acid 45 in CR1 is replaced by glycine (Gly) and 7 amino acid residues (DLTCHEA) in CR2 are replaced by 7 glycine residues (GGGGGGG). The number (28592-30470) indicated in the deleted E3 region represents positions in Ad5 genome. In FIGS. 1q-1v, TSP represents a tumor specific promoter, preferably hTERT (human telomere reverse transcriptase) promoter, m-hTERT (see SEQ ID NO:33) or E2F promoter. F435-kox(p65) describes the existence of F435-kox or F435-p65. In figures, Δ denotes deletion, and ITR, ψ, Ad, CMV and IX represent inverted terminal repeat, package signal sequence, adenovirus, CMV promoter and a gene encoding the protein IX of adenovirus, respectively. F435-kox and F435-p65 represent the DNA binding domain of SEQ ID NO:2 linked to kox domain sequence and p65 domain sequence.

FIGS. 3a and 3b represent the expression of VEGF-A infected with Ad-ΔE1GFP-p65. The concentration of VEGF-A in the culture supernatant was measured by ELISA. FIG. 3a, VEGF-A expression by U343. FIG. 3b, VEGF-A expression by AoSMC and CASMC.

FIGS. 4a-4b represent that the replication incompetent adenovirus encoding F435-kox or F435-p65 inhibits or promotes VEGF-induced tube formation of HUVEC. HUVECs were plated on Matrigel-coated plates at a density of $2 \times 10^5$ cells/well and then incubated with the conditioned media of Ad-ΔE1GFP or Ad-ΔE1GFP-kox infected U343 at 30 MOI for 48 hrs, in the case of U87MG, 50 MOI and 72 hrs (FIG. 4a). The conditioned media of U343 infected with 100 MOI Ad-ΔE1GFP or Ad-ΔE1GFP-p65 for 36 hrs and that of CASMC infected with 500 MOI for 36 hrs were used (FIG. 4b). After 18-24 hrs, microphotographs were taken (×40).

FIGS. 8a and 8b represent anti-tumor effects and survival rate of adenoviruses expressing F435-kox. Tumors were established by subcutaneous implantation of $1 \times 10^7$ cells and allowed to grow to 60-70 mm$^3$. Nude mice with established tumors were randomized into five treatment groups of seven animals each. Each group received intratumoral injection of adenovirus ($5 \times 10^8$ PFU of adenovirus in 30 µl of PBS) on days 1, 3, and 5. Tumor growth was monitored on a two-day interval by measuring the short length (w) and the long length (L) of the tumor. Tumor volume was estimated on the basis of the following formula (FIG. 8a): tumor volume (mm$^3$)=0.523×Lw$^2$. FIG. 8b represents survival curve analysis. The percentage of surviving mice was determined by monitoring the death of mice. Tumor size over 2000 mm$^3$ was regarded as death.

Figure 1K:
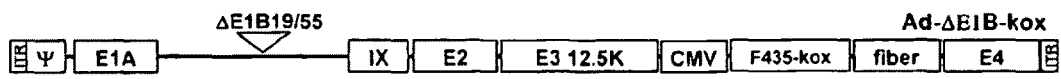
Figure 1L:
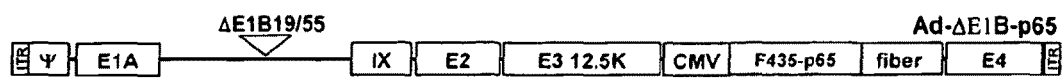
Figure 1M:
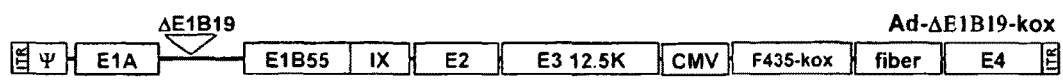
Figure 1N:
Figure 1O:
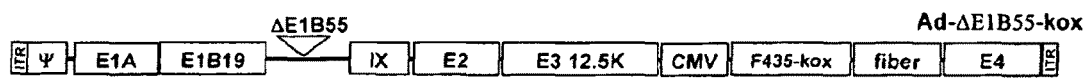
Figure 1P:
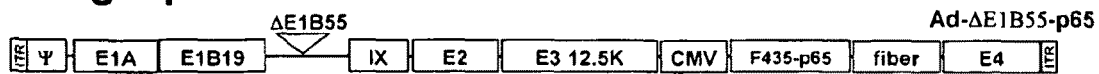
Figure 1T:
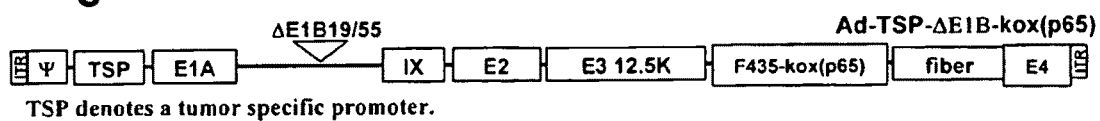
Figure 1U:
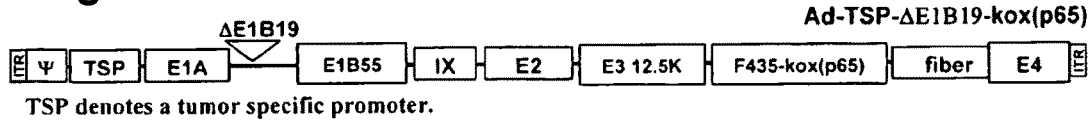
Figure 1V:
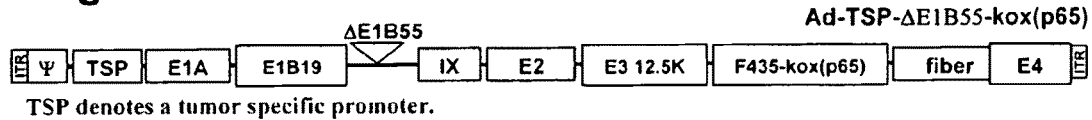

The following specific examples are intended to be illustrative of the invention and should not be construed as limiting the scope of the invention as defined by appended claims.

EXAMPLES

Materials and Methods

1. Cell Lines and Cell Culture

Cell lines used include human brain cancer cell lines (U343, U87MG), human coronary artery smooth muscle cell (CASMC) and human aortic smooth muscle cell (AoSMC). The brain cancer cell lines and smooth muscle cells were purchased from the American Type Culture Collection (ATCC, Manassas, Va., USA) and Cambrex (Cambrex Bio Science, Walkersville, Md., USA), respectively. Human umbilical vascular endothelial cells (HUVEC) were obtained from Dr. Y. G. Kwon (Yonsei University, South Korea). HEK293 cell lines (ATCC) containing the E1 region gene (early expression gene of adenoviruses) were utilized as adenovirus-producing cells.

The brain cancer cell lines were cultured in Dulbecco's modified Eagle's medium (DMEM; Gibco BRL) supplemented with 10% fetal bovine serum (Gibco-BRL, Grand Island, N.Y., USA), penicillin (100 Mimi), and streptomycin (100 μg/ml, Gibco-BRL) under 5% $CO_2$ incubator at 37° C. The smooth muscle cells were cultured in SmGM-2 (Cambrex) supplemented with 5% FBS, 2 ng/ml human fibroblast growth factor-B, 0.5 ng/ml human epidermal growth factor, 50 μg/ml gentamicin, 50 ng/ml amphotericin-B and 5 μg/ml bovine insulin. Smooth muscle cells at passage 5-8 were only used for experiments. The HUVEC cells were cultured in M199 (Invitrogen, Carlsbad, Calif., USA) supplemented with 20% FBS, 100 U/ml penicillin, 100 μg/ml streptomycin, 3 ng/ml basic fibroblast growth factor (Upstate Biotechnology, Lake Placid, N.Y., USA) and 5 units/ml heparin. Cells at passage 3-5 were only used for experiments.

2. Experimental Animals

Rat aorta ring sprouting assay was carried out using 6-week-old Sprague-Dawley male rats purchased from SLC (Japan SLC, Inc., Japan). In vivo anti-cancer effects were verified using 6-8 week-old male nude mice (BALB/c-nu) from SLC. All animals were maintained at 22±2° C. in a humidified atmosphere of 55-60% with dark/light cycle of 12 hr:12 hr. All animals were permitted to freely access pathogen-free feeds (Central Experimental Animals, Inc. Seoul, Korea) and water.

3. Generation and Titration of Adenoviruses Expressing VEGF-A Promoter Specific Zinc Finger Protein Zinc finger protein plasmids, F435-kox and F435-p65 (Toolgen, Inc., Daejeon, Korea) to effectively repress and promote VEGF-A transcription were introduced into adenoviral E3 shuttle vector pSP72ΔE3 (*Cancer Gene Therapy*, 12:61-71 (2005)) to generate pSP72013-F435-kox and pSP72ΔE3-F435-p65, respectively. The nucleotide sequence of F435 used is set forth in SEQ ID NO:8, and the nucleotide sequences of p65 domain and KOX domain used are set forth in SEQ ID NOs:9 and 10, respectively. To construct replication incompetent adenoviruses expressing GFP (green fluorescence protein) and zinc finger protein, the pSP72ΔE3-F435-kox and pSP72ΔE3-F435-p65 E3 shuttle vectors were linearized by digestion with PvuI and ScaI, respectively. The GFP gene was introduced into replication incompetent adenovirus dl324 with deleted E1 and E3 regions (obtained from Dr. Verca, University of Fribourgh, Switzerland; Heider, H. et al., *Biotechniques*, 28(2):260-265, 268-270 (2000)) to generate pAd-ΔE1GFP, after which it was linearized with SpeI. The linearized vectors were cotransformed into *E. coli* BJ5183 (obtained from Dr. Verca, University of Fribourgh, Switzerland; Heider, H. et al., *Biotechniques*, 28(2):260-265, 268-270 (2000)) to induce homologous recombination, finally providing replication incompetent adenoviral vectors pAd-ΔE1GFP-kox and pAd-ΔE1GFP-p65 expressing both GFP and VEGF-A promoter specific zinc finger protein.

To construct tumor-specific oncolytic adenoviruses expressing VEGF-A promoter specific zinc finger protein, the pSP72ΔE3-F435-kox adenoviral E3 shuttle vector was linearized with PvuI and then cotransformed into *E. coli* BJ5183 together with SpeI-digested pAd-ΔB7 adenovirus total vector (tumor-specific oncolytic adenovirus having mutated Rb binding site in E1 and deleted E1B 19 kDa and E1B 55 kDa regions: KCCM-10569), generating tumor-specific oncolytic pAd-ΔB7-kox vector.

The homologous recombinant plasmids were digested with HindIII for verifying homologous recombination and then digested with PacI, followed by transforming into HEK293 cell lines to produce adenoviruses. As controls, Ad-ΔE1GFP having the GFP gene in deleted E1 region and Ad-ΔB7 having mutated Rb binding site in E1A region and deleted E1B 19 kDa and E1B 55 kDa regions were propagated in HEK293 cell lines, concentrated using CsCl gradient and purified. Their titers (plaque forming unit; PFU) were analyzed by limiting titration assay.

4. Analysis of Change in VEGF-A Expression Level

To analyze VEGF-A expression level regulated by adenoviruses expressing VEGF-A promoter specific zinc finger protein, enzyme-linked immunosorbent assay (ELISA) was conducted. First, to verify the repression of VEGF-A expression, the brain cancer cell lines U343 and U87MG ($1\times10^6$ cells) were transferred to 25T flask, and one day later were infected with adenoviruses at various multiplicity of infection (MOI) for 4 hr, followed by changing medium with fresh 5% DMEM. At the time of 48 hr, 72 hr and 96 hr after viral infection, medium was collected. Prior to 30 hr of medium collection, the cells were subjected to starvation for 6 hr with DMEM with no FBS and then cultured for 24 hr in DMEM containing 1% FBS. The collected medium was centrifuged at 3000 rpm and its supernatant was harvested for VEGF-A ELISA. The remaining cells were lyzed using 150 μl of cold lysis buffer and centrifuged at 10,000×g for 15 min to separate proteins. The quantification of proteins in cells was carried out using a protein analysis kit (Bio-Rad, Hercules, Calif., USA). The quantities of VEGF-A determined by ELISA were calibrated with quantities of proteins in cells. To analyze the promotion of VEGF-A expression, U343 cell line ($6\times10^5$ cells), CASMC and AoSMC ($2.5\times10^5$ cells) were plated onto 6-well plate and one day later were infected with adenoviruses at various multiplicity of infection (MOI) for 4 hr, followed by changing medium with fresh 5% DMEM and SmGM-2 containing 1% FBS, respectively. At the time of 24 hr, 36 hr and 48 hr after medium change, medium was collected for ELISA analysis described above.

5. Tube Formation Assay

To verify whether the tube formation of vascular endothelial cells is altered by increase or decrease in VEGF-A expression due to the expression of VEGF-A promoter specific zinc finger protein, the tube formation assay was performed using HUVEC cells. 250 μl of growth factor-reduced Matrigel (Collaborative Biomedical Products, Bedford, Mass., USA) was plated onto 24-well plate on ice and subjected to polymerization for 30 min at 37° C. HUVEC (3-5 passage cultures) cells were cultured for starvation in M199 medium containing 1% FBS for 6 hr and trypsinized, followed by cell counting. For VEGF-A expression repression experiments, serum starvation-pretreated HUVEC ($2\times10^5$ cells) cells were incubated with U87MG conditioned media collected after 72-hr infection with Ad-ΔE1GFP or Ad-ΔE1GFP-kox at 50 MOI or U343 conditioned media collected after 48-hr infection with Ad-ΔE1GFP or Ad-ΔE1GFP-kox at 30 MOI and plated onto 24-well plate containing matrigel for culturing. For VEGF-A expression promotion experiments, HUVEC cells were incubated with the conditioned media of U343 infected with Ad-ΔE1GFP or Ad-ΔE1GFP-p65 at 100 MOI or the conditioned media of CASMC infected with Ad-ΔE1GFP or Ad-ΔE1GFP-p65 at 500 MOI. As a positive control, 40 ng/ml of VEGF-A protein (Upstate Biotechnology, Lake Placid, N.Y., USA) was used. At the time of 18-24 hr after incubation, cells were removed of culture media and washed twice with PBS, followed by observation of tube formation under microscope.

6. Ex Vivo Aorta Ring Sprouting Assay

For evaluate the repression or promotion of blood vessel formation on the expression of VEGF-A promoter specific zinc finger protein, the aorta ring sprouting assay was carried out. Aorta was separated from 6-week old Sprague Dawley rat, removed of fibro-adipose tissues and sectioned to 1-mm thick rings. 120 μl of matrigel was plated onto each well of cold 48-well plate and subjected to polymerization for 10 min at 37° C. Aorta rings was placed on each well and 50 μl of matrigel was overlaid. After 30 min, matrigel was solidified and 250 μl of the conditioned medium used in the tube formation assay was introduced into each well for incubation. As a positive control, 40 ng/ml of VEGF-A protein was used. On day 6, 9 and 12 after incubation, blood vessels generated from aorta rings were imaged by optical imaging technique[39]. The vessel formation was evaluated in a double-blinded manner in which positive control (most positive) was graded 5 and no vessel formation group (least positive) graded 0. Each experimental group for aorta ring sprouting assay was evaluated using 12 aorta rings.

7. Analysis of Cytopathic Effects of Tumor-Specific Adenoviruses Expressing Zinc Finger Protein to Repress VEGF-A Transcription To assess whether the expression of VEGF-A promoter specific zinc finger protein affects adenoviral replication, the cytopathic effect (CPE) reflecting viral replication was analyzed. Human cancer cell lines such as brain cancer cell line (U343), liver cancer cell line (Hep1), cervical cancer cell line (C33A) and pulmonary cancer cell line (A549) were plated onto 24-well plates and then infected with Ad-ΔE1LacZ, Ad-ΔB7, or Ad-ΔB7-kox adenoviruses at various MOIs. At the moment that cells infected with viruses at low MOI exhibited complete cell lysis, medium was discarded and cells on the plate were then stained 0.5% crystal violet (in 50% methanol).

8. In Vivo Antitumor Effects

Tumors were implanted on the abdomen of 6-8 week-old nude mice by subcutaneous injection of 1×10⁷ human brain cancer cells (U87MG). When tumors reached a range of 60-70 mm³, Ad-ΔE1GFP, Ad-ΔE1GFP-kox, Ad-ΔB7 or Ad-Δ137-kox adenoviruses (5×10⁸ PFU) or PBS were administered intratumorally every other day three times. The size of tumors was measured every other day using a caliper. Tumor volume was calculated using the following formula: volume (mm³)=(minor axis mm)²×(major axis mm)×0.523

9. Analysis of Angiogenesis Repression in Tumors by Oncolytic Adenoviruses Expressing Zinc Finger Proteins to Inhibit VEGF-A Transcription Tumors were implanted on the abdomen of 6-8 week-old nude mice by subcutaneous injection of human brain cancer cells (U343 or U87MG). When tumors reached a range of 100-120 mm³, Ad-ΔB7 or Ad-ΔB7-kox adenoviruses (5×10⁸ PFU) or PBS were administered intratumorally every other day three times. Ten days later, tumors were isolated and fixed in IHC Zinc fixative (Formalin-free) (BD Biosciences Pharmingen, San Diego, Calif., USA) for preparing paraffin blocks. The paraffin blocks prepared were cut into 4-μm slides and immersed successively in xylene, and 100%, 90% and 70% ethanol for deparafinization, followed by staining with hematoxylin and eosin (H&E). To elucidate whether angiogenesis in tumor tissues were repressed by the expression of zinc finger protein to inhibit VEGF-A transcription, immunohistochemical staining was performed using rat anti-mouse CD31 monoclonal antibodies (MEC13.3; BD Biosciences Pharmingen) specifically recognizing the vascular endothelial cell specific antigen CD31. Endogenous peroxidase in 4-μm slides was blocked with 3% $H_2O_2$ solution. The tissue slides was incubated with CAS-BLOCK (Zymed, San Francisco, Calif., USA) for 30 min to block non-specific reactions, and then incubated with the primary α-CD31 antibody. Then, the slides were incubated with biotin-conjugated polyclonal anti-rat IgG antibody (BD Biosciences. Pharmingen) as the secondary antibody and the expression of CD31 was determined using DAB (DakoCytomation, Carpinteria, Calif., USA).

10. Blood Vessel Counting in Tumors

Blood vessels shown to be positive to vascular endothelial cell specific antigen CD31 (platelet endothelial cell adhesion molecule 1) were first observed at low magnification to obtain photographs and their number was determined at 100× magnification. From three slides, each five visual fields were selected and the number of blood vessels was determined. The mean values were calculated as representative value.

Results

1. Generation of Adenoviruses Expressing VEGF-A Promoter Specific Zinc Finger Protein and Evaluation of VEGF-A Expression Two types of adenovirus (Ad-ΔE1GFP-kox and Ad-ΔE1GFP-p65) expressing zinc finger protein, F435-kox and F435-p65, respectively, which specifically bind to VEGF-A promoter to repress or promote the transcription of VEGF-A, were constructed (FIGS. 1a-1c).

Figure 2:
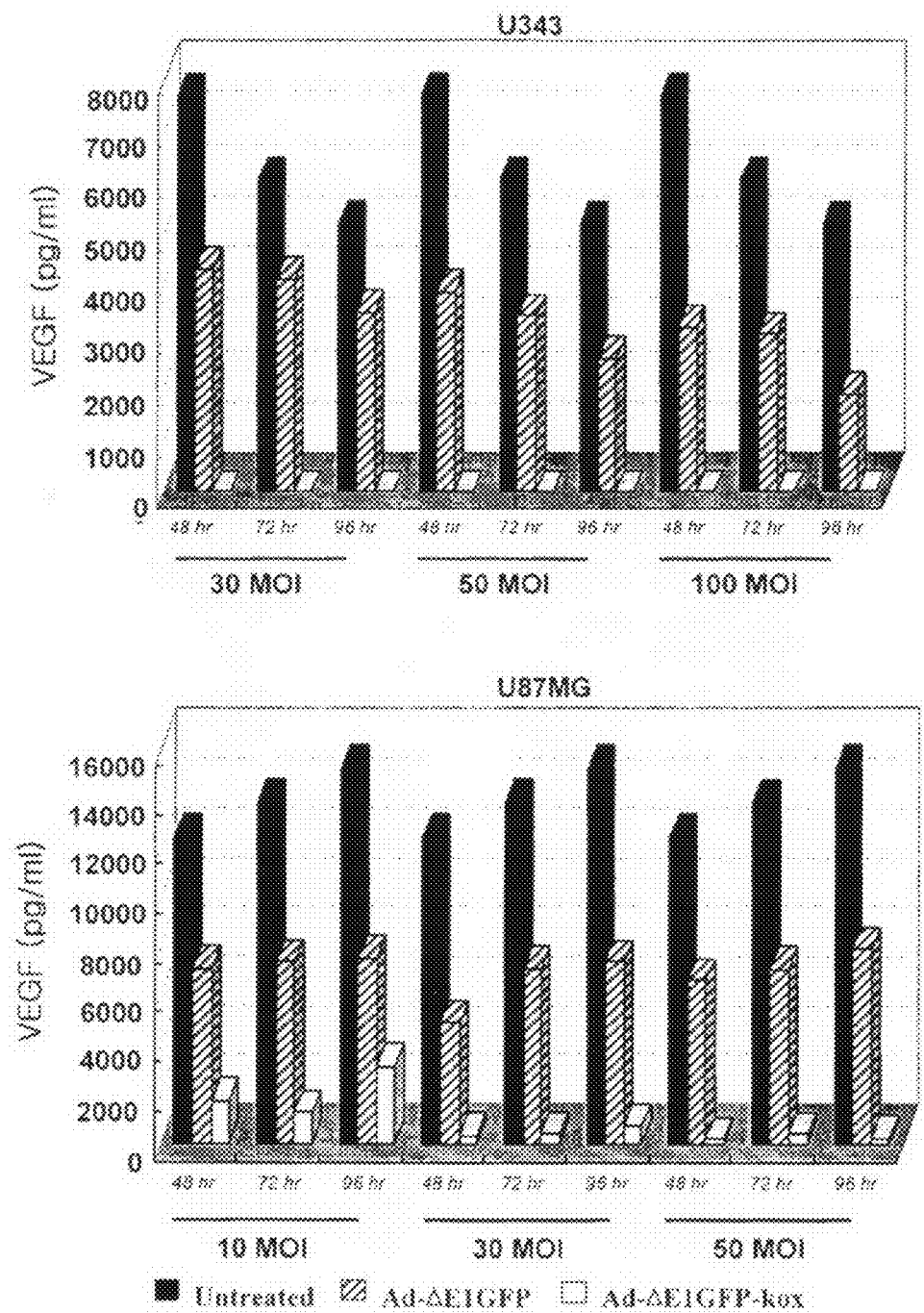
FIG. 2 represents the expression of VEGF-A by U343 and U87MG infected with Ad-ΔE1GFP-kox.
Figure 3B:
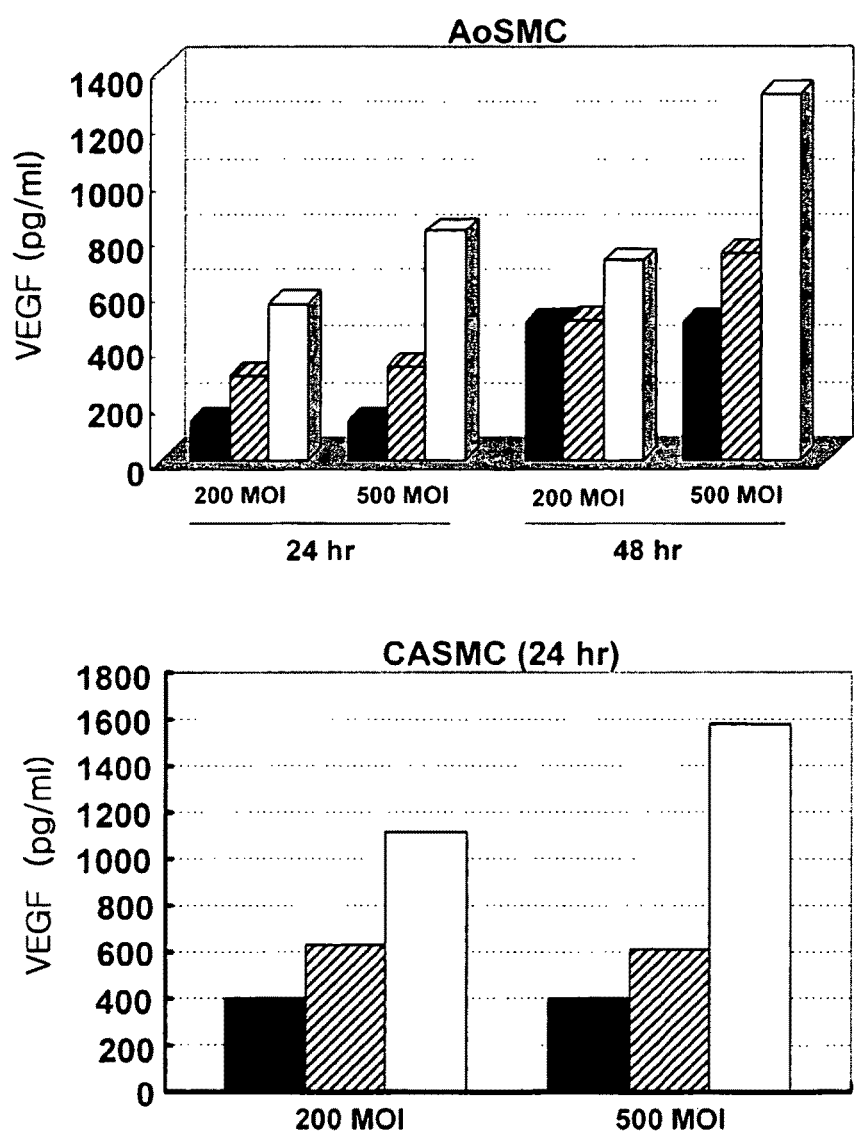

Because it has been already reported that replication incompetent adenoviruses expressing adenoviral early gene E1A could suppress VEGF expression[40], the replication incompetent Ad-ΔE1GFP-kox adenovirus lacking E1A and expressing both F435-kox and GFP was constructed to verify VEGF-A expression patterns on F435-kox expression. Human brain cancer cell lines U87MG and U343A exhibiting higher VEGF expression level were infected with ΔE1GFP-kox and media were collected for ELISA analysis to quantify VEGF-A expression. It was revealed that the Ad-ΔE1GFP-kox adenovirus inhibits significantly VEGF-A expression in two type cells (FIG. 2). In U343 cell line, the expression of VEGF-A was completely inhibited by the Ad-ΔE1GFP-kox adenovirus at more than 30 MOI. In U87MG cell line, the VEGF-A protein was not detected in the medium infected with the Ad-ΔE1GFP-kox adenovirus at more than 30 MOI. In particular, U87MG cell line infected for 96 hr with Ad-ΔE1GFP-kox exhibited the expression level of VEGF-A (0.2 ng/ml) about 40-fold lower than that (7.9 ng/ml) infected with control virus Ad-ΔE1GFP. These results demonstrate that adenoviruses carrying F435-kox could inhibit the expression of the target gene, the VEGF-A gene by 97.5%. In the meantime, it has been already suggested that F435-kox carried in plasmid rather than adenoviruses inhibited the expression of the VEGF gene by 75% (Kwon et al. *Nucleic Acids Research* 33, e74 (2005)).

Where human brain cancer cell line U343 or human muscle cell line CASMC and AoSMC was infected with the Ad-ΔE1GFP-p65 adenovirus expressing F435-p65 to promote transcription of VEGF-A, the expression of the VEGF-A increased as a function of increasing the titers of adenoviruses and the incubation time (FIGS. 3a and 3b). AoSMC cell line infected with Ad-ΔE1GFP-p65 exhibited the expression level of VEGF-A (819 pg/ml) about 2.5-fold higher than that that (340 pg/ml) infected with control virus Ad-ΔE1GFP at 500 MOI.

2. Influence of VEGF-A Promoter Specific Zinc Finger Protein-Expressing Adenoviruses on Angiogenesis To verify whether the differentiation potential of vascular endothelial cells is altered by increase or decrease in VEGF-A expression due to the expression of VEGF-A promoter specific zinc finger proteins (F435-kox and F435-p65), the tube formation assay was performed using HUVEC cells. U343 or U87MG cell lines were infected for 48-72 hr with either Ad-ΔE1GFP or Ad-ΔE1GFP-kox adenoviruses at 30 MOI or 50 MOI and HUVEC cells were then cultured in the conditioned medium. It was observed that HUVEC cells cultured in either cell culture medium not infected or cell culture medium infected with Ad-ΔE1GFP generated large and thick tubes. In contrast, HUVEC cells cultured in the conditioned medium infected with the Ad-ΔE1GFP-kox adenovirus exhibited far poor angiogenesis to form much thinner and partially broken tubes (FIG. 4a).

Figure 4B:
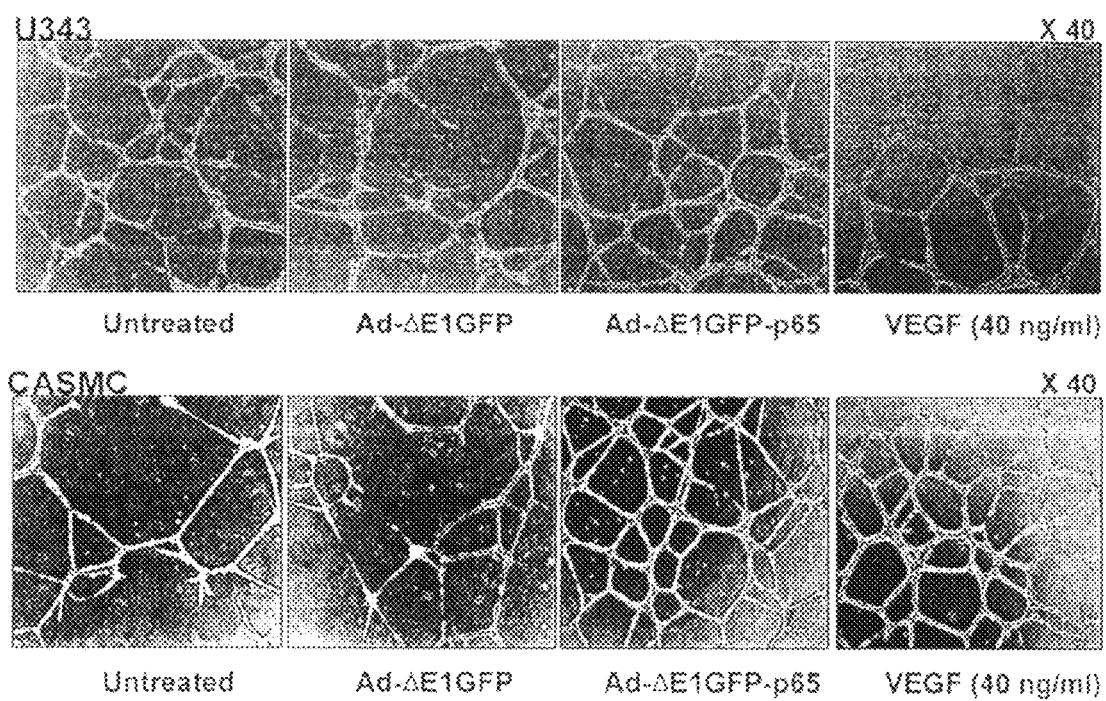

Meanwhile, U343 or CASMC cell lines were infected for 36 hr with the Ad-ΔE1GFP-p65 adenoviruses at 100 MOI (U343) or 500 MOI (CASMC) and HUVEC cells were then cultured in the conditioned medium. HUVEC cells cultured in the conditioned medium infected with ΔE1GFP-p65 generated much thicker and less broken tubes compared those cultured in either cell culture medium not infected or cell culture medium infected with Ad-ΔE1GFP (FIG. 4b). In particular, HUVEC cells cultured in the conditioned medium infected with ΔE1GFP-p65 were analyzed to show active angiogenesis similar to those treated with 40 ng/ml of the VEGF-A protein.

Figure 5A:
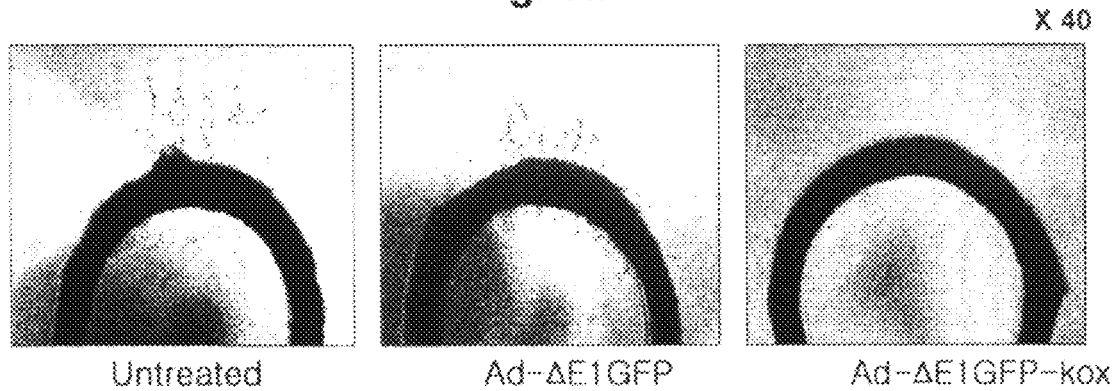
FIGS. 5a-5b demonstrate that the replication incompetent adenovirus encoding F435-kox inhibits VEGF-induced vessel sprouting ex vivo. Aortas in Matrigel were treated with the conditioned media of Ad-6E1GFP or Ad-ΔE1GFP-kox infected U87MG at 50 MOI for 72 hrs (FIG. 5a). Ad-ΔE1GFP-kox blocked VEGF-induced vessel sprouting (FIG. 5b). The assay was scored from 0 (least positive) to 5 (most positive) and the data are presented as mean (n=7) ±SE.
Figure 5B:
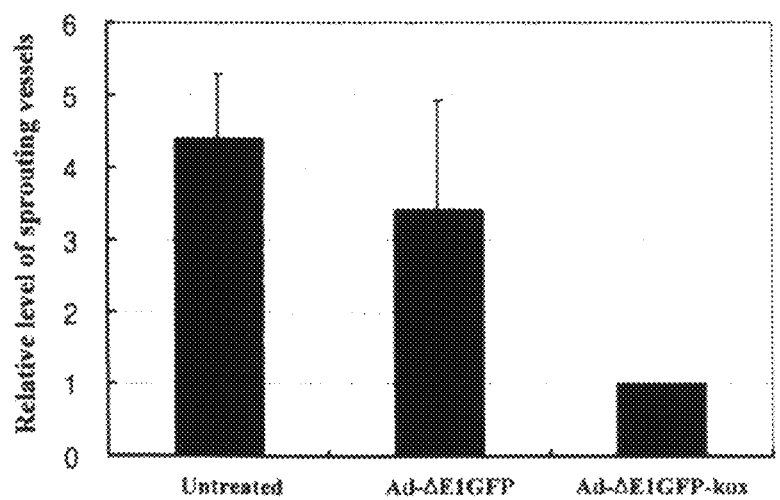
Figure 6A:
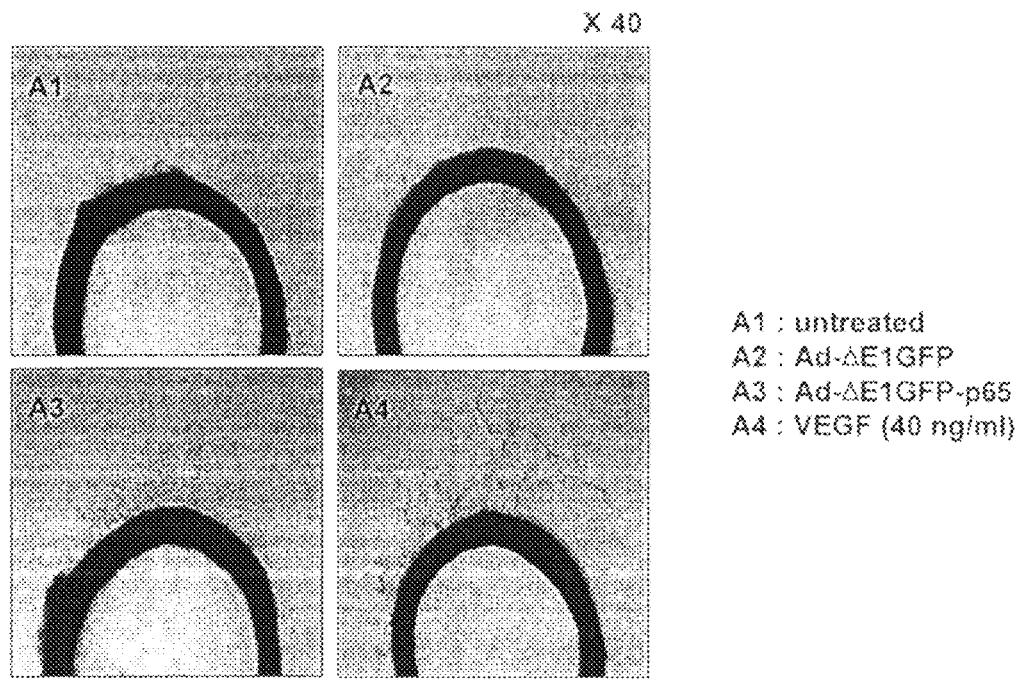
FIGS. 6a-6d represent that the replication incompetent adenovirus encoding F435-p65 promotes VEGF-induced vessel sprouting ex vivo. Aortas in Matrigel were treated with the conditioned media of U343 infected with 100 MOI Ad-ΔE1GFP or Ad-ΔE1GFP-p65 for 36 hrs (FIG. 6a). Ad-ΔE1GFP-p65 promoted VEGF-induced vessel sprouting. The assay was scored from 0 (least positive) to 5 (most positive) and the data are presented as mean (n=5)±SE (FIG. 6b). The conditioned media of CASMC infected with 500 MOI for 36 hrs were treated. Representative aortic rings were photographed (×40) (FIG. 6c). The assay was scored from 0 (least positive) to 5 (most positive) and the data are presented as mean (n=8)±SE (FIG. 6d).
Figure 6B:
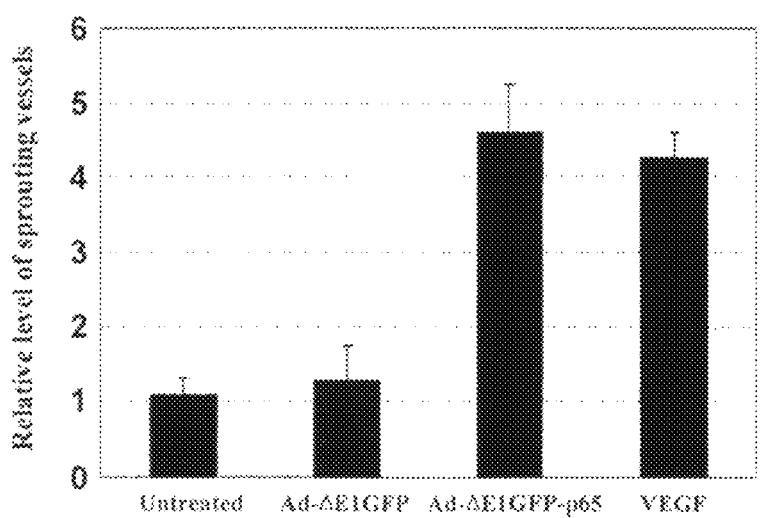
Figure 6C:
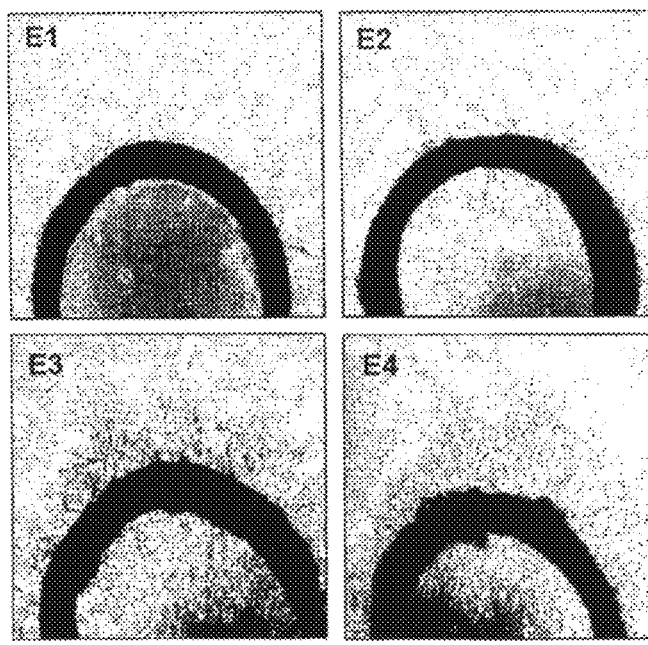
Figure 6D:
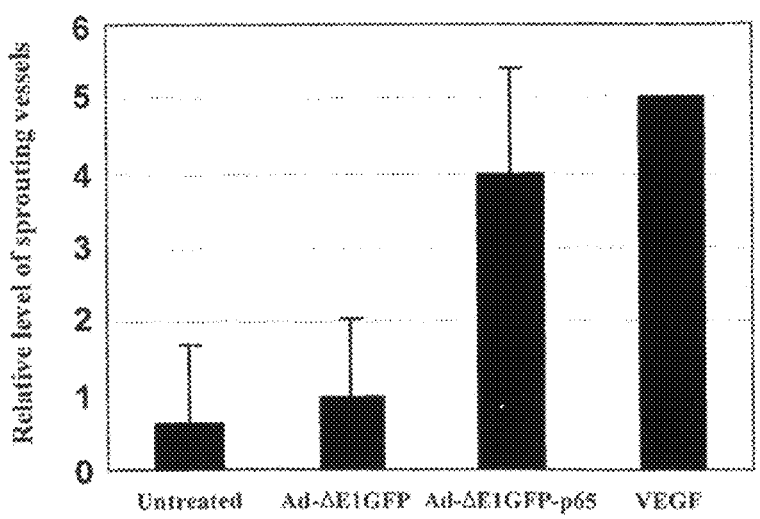

To confirm ex vivo the difference in angiogenesis potentials evaluated above, the vessel sprouting assay was performed using rat aorta. U87MG cells were infected for 72 hr with Ad-ΔE1GFP or Ad-ΔE1GFP-kox at 50 MOI and aorta rings were incubated with the conditioned medium for 7 days. As a result, it was observed that aorta ring cultured in the conditioned medium infected with the Ad-ΔE1GFP-kox adenovirus exhibited little or no vessel sprouting (FIG. 5a). However, aorta ring cultured in either medium not infected or medium infected with Ad-ΔE1GFP showed vessel sprouting. For confirming quantitatively the vessel sprouting potentials, the vessels formed were analyzed in a double-blinded manner in which the positive control (most positive) was scored as 5 and the no-sprouting group (least positive) as 0. Where aorta was cultured in medium not infected and medium infected with Ad-ΔE1GFP, the scores were determined as 4.4±0.9 and 3.4±1.5, respectively, indicating the occurrence of active angiogenesis. In contrast, where aorta was cultured in the conditioned medium infected with the Ad-ΔE1GFP-kox adenovirus, the score was determined as 1.0±0.0, indicating significantly suppressed angiogenesis (FIG. 5b).

Where aorta was treated with the conditioned medium infected with the Ad-ΔE1GFP-p65 adenovirus, more active vessel sprouting was observed compared with those treated with either the medium not infected or the medium infected with Ad-ΔE1GFP (FIG. 6). The scoring quantitative analysis revealed that the score for the U343 cell culture medium infected with the Ad-ΔE1GFP-kox adenovirus was determined as 4.6±0.65, indicating the occurrence of active vessel sprouting events. However, the scores for the U343 cell culture medium not infected and the U343 cell culture medium infected with Ad-ΔE1GFP were determined as 1.1±0.22 and 1.3±0.45, respectively. Experiments using CASMC cell culture medium showed similar results.

Figure 7:
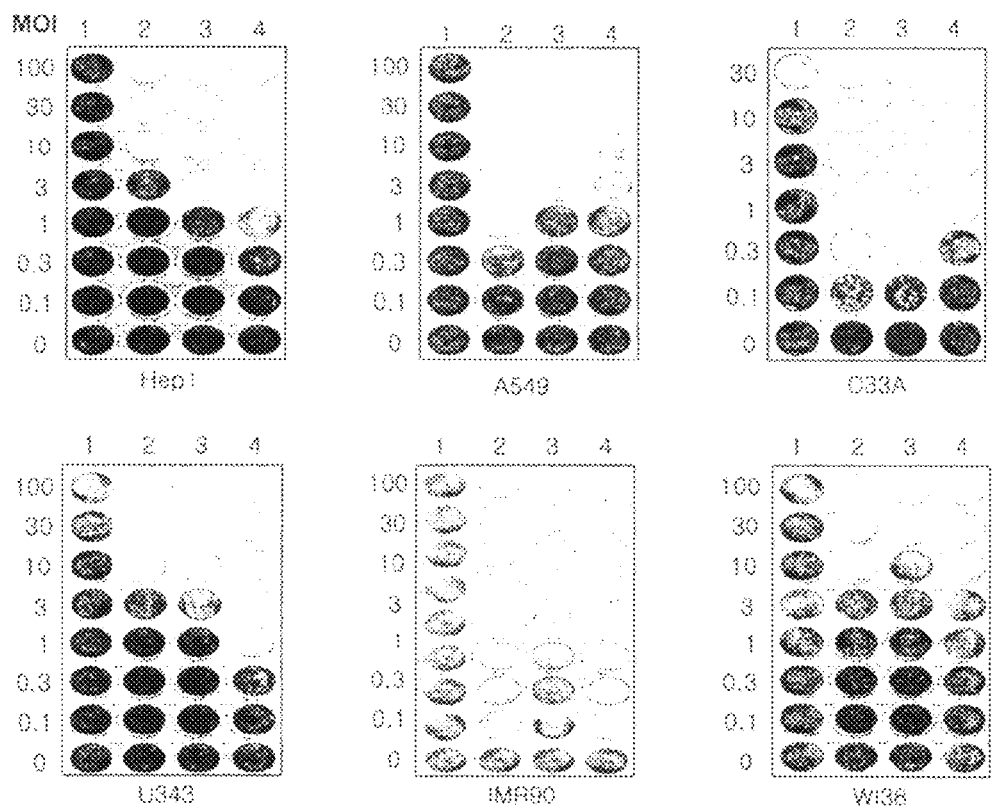
FIG. 7 shows cytopathic effects (CFE) of Ad-ΔB7-kox in vitro. Cells were infected with Ad-ΔE1LacZ, Ad-ΔB7, Ad-ΔB7-kox, and Ad-XC at the indicated MOI. Replication incompetent adenovirus, Ad-ΔE1LacZ and wild type adenovirus Ad-XC served as controls. At 4-10 days after infection, cells remaining on the plates were fixed and stained with crystal violet.

3. Cytopathic Effects of Tumor-Specific Adenoviruses Expressing F435-kox to Repress the Expression of VEGF-A The decrease in angiogenesis potential by repression of VEGF-A expression has been known to suppress tumor growth. The Ad-ΔB7-kox adenovirus expressing F435-kox and the oncolytic tumor-specific Ad-ΔB7 as control were constructed (FIGS. 1d and 1e). First, to verify whether the expression of F435-kox inhibits replication of adenoviruses, various cancer cells and normal cells were infected Ad-ΔE1LacZ, Ad-ΔB7, Ad-ΔB7-kox or Ad-XC and then CPE assay was performed to analyze cell lysis due to viral replication (FIG. 7). Since the replication of adenoviruses does not occur in cells infected with the replication incompetent Ad-ΔE1LacZ adenovirus as a negative control, the cell killing effects were not detected. In the case that cells were infected with replication competent Ad-ΔB7 or Ad-ΔB7-kox adenoviruses, the cytopathic effects increased as the titer of viruses increase. In particular, the cytopathic effects of F435-kox expressing Ad-ΔB7-kox were analyzed to be similar to those of Ad-ΔB7 as control virus in all cell lines (Hep1, C33A, U343 and IMR90) except for A549 and WI38.

4. In Vivo Anti-Tumor Effects of Tumor-Specific Oncolytic Adenoviruses Expressing F435-kox to Repress the Expression of VEGF-A To verify in vivo anti-tumor effects of adenoviruses expressing F435-kox to inhibit VEGF-A expression, tumors were implanted on the abdomen of nude mice by subcutaneous injection of human brain cancer cells (U87MG). When tumors reached a range of 60-70 mm$^3$, Ad-ΔE1GFP, Ad-ΔE1GFP-kox, Ad-ΔB7 or Ad-ΔB7-kox adenoviruses ($5 \times 10^8$ PFU) or PBS were administered intratumorally every other day three times and tumor growth was observed (FIG. 8a). Tumors treated with PBS as a negative control abruptly grown and reached an average size of about 2789.4±337.4 mm$^3$ on day 22 post-treatment. In contrast, tumors treated with viruses (replication incompetent Ad-ΔE1GFP-kox adenovirus expressing F435-kox, tumor-specific oncolytic Ad-ΔB7 or Ad-ΔB7-kox adenoviruses) were substantially delayed in their growth in all human xenograft models treated. More specifically, nude mice treated with Ad-ΔE1GFP-kox, Ad-ΔB7 and Ad-ΔB7-kox reached an average tumor volume of 1046.4±163.5 mm$^3$, 942.9±383.4 mm$^3$ and 399.9±158.3 mm$^3$, respectively on day 22 post-treatment, evidently showing excellent anti-tumor effects due to angiogenesis inhibition of tumor-specific oncolytic adenoviruses expressing F435-kox. In particular, nude mice administered with Ad-ΔB7 reached an average tumor volume of more than 1000 mm$^3$ on day 26 post-treatment; nude mice treated with Ad-ΔB7-kox reached an average tumor volume of less than 900 mm$^3$ even on day 36 post-treatment, which urge us to reason that the recombinant adenoviruses of this invention have higher anti-tumor potential than conventional oncolytic adenoviruses.

The survival rate of tumor bearing nude mice was examined. 100% of the animals treated with the Ad-ΔB7-kox adenovirus were still viable 50 days after the beginning of the treatment, whereas less than 50% of Ad-ΔE1GFP-kox or Ad-ΔB7-treated mice were viable on day 28 or 36 post-treatment. These results clearly show that F435-kox-expressing adenoviruses of the present invention can confer significant survival benefits and tumor reduction in vivo (FIG. 8b).

Figure 9A:
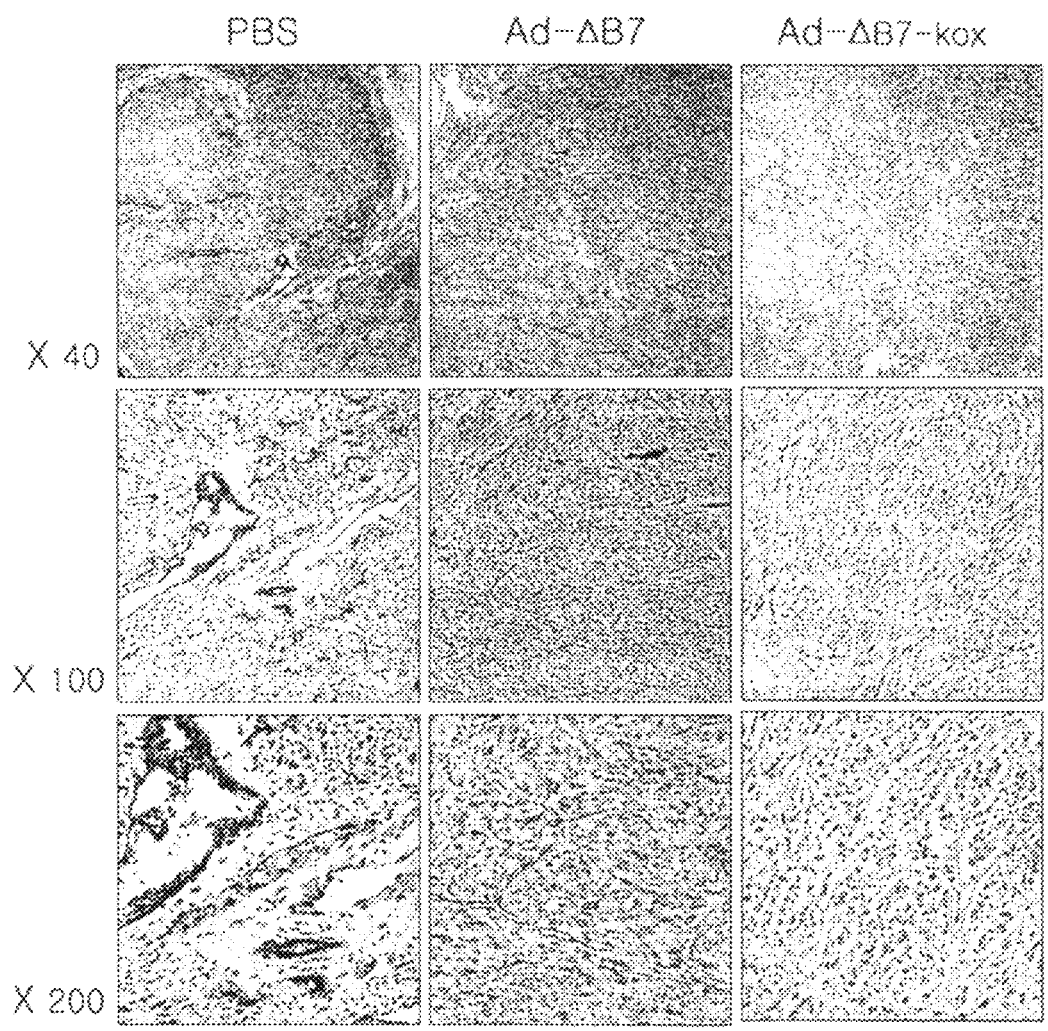
FIGS. 9a-9c represents histological assessment of angiogenesis in the tumor tissue treated with Ad-ΔB7-kox. Ten days following third adenovirus administration, mice were sacrificed and the tumor tissues were embedded in paraffin. Paraffin blocks were cut and stained with an antibody against platelet endothelial cell adhesion molecule-1. U343 tumor tissue (FIG. 9a); and U87MG tumor tissue (FIG. 9b). Representative CD31 stained tissues were photographed. Quantification of vessel numbers in tumor tissues (FIG. 9c). The data are presented as mean (n=3)±SE.
Figure 9B:
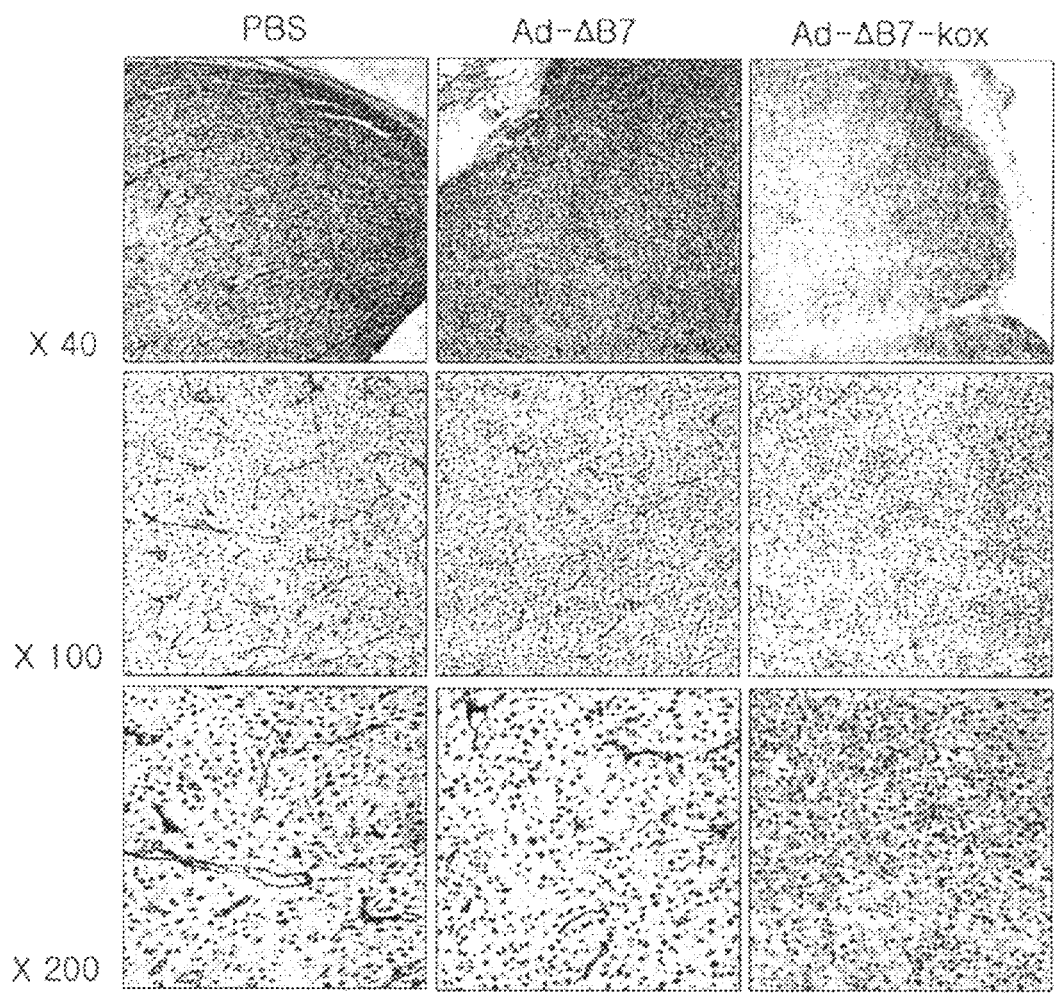
Figure 9C:
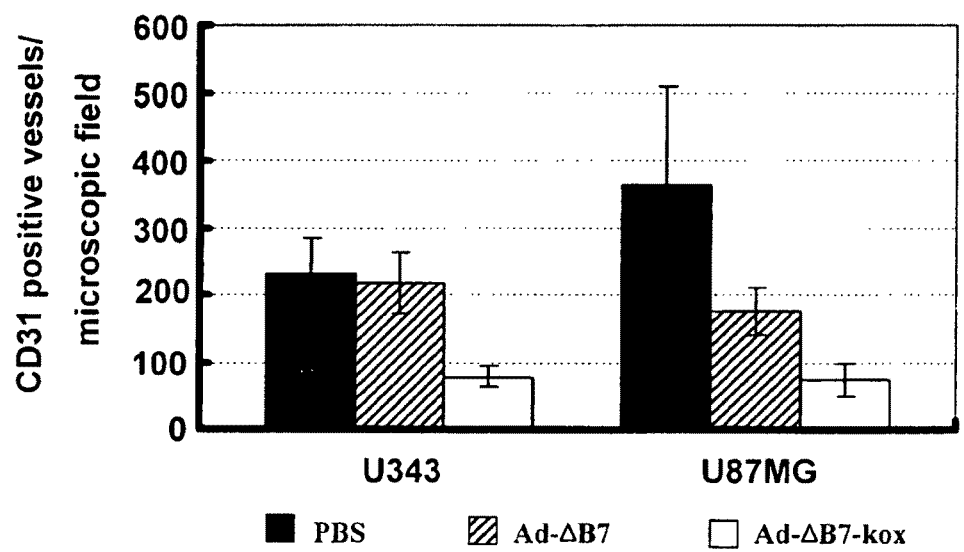

5. Angiogenesis Patterns in Tumors Treated with Adenoviruses Expressing F435-kox to Repress VEGF-A Expression Tumors were implanted on the abdomen of nude mice by subcutaneous injection of human brain cancer cells (U343 or U87MG). Then, Ad-ΔB7 or Ad-ΔB7-kox adenoviruses or PBS were administered intratumorally three times. Ten days later, tumors were isolated for immunohistochemical staining for vascular endothelial cell-specific antigen CD31. As a result, it was clearly observed that the angiogenesis of tumors treated with Ad-ΔB7 or Ad-ΔB7-kox was suppressed (FIGS. 9a and 9b). In particular, the number of blood vessels (78±15) in U343 tumor treated with Ad-ΔB7-kox decreased by three-fold compared to that treated with Ad-ΔB7 (217±45). The number of vessels in U87MG tumor treated with Ad-ΔB7-kox decreased by about 2.5-fold compared to that treated with Ad-ΔB7 (FIG. 9c).

As described hereinabove, the present invention provides a recombinant adenovirus capable of regulating angiogenesis. In addition, the present invention provides a pharmaceutical composition or method for preventing or treating an angiogenesis-associated disease. The recombinant adenovirus of this invention capable of regulating the expression of the VEGF-A gene represses or promotes the expression of all isoforms of VEGF-A and provides promising therapeutics to prevent or treat angiogenesis-associated diseases. In particular, the recombinant adenoviruses carrying transcription inhibitory domains selectively suppress angiogenesis in tumor to dramatically elevate anti-tumor effects. Furthermore, the recombinant adenoviruses carrying transcription inhibitory domains can induce tumor cell-killing effects even at lower titers, contributing to significant safety in human application.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Senger D R, Galli S J, Dvorak A M, Perruzzi C A, Harvey V S and Dvorak H F. Tumor cells secrete a vascular permeability factor that promotes accumulation of ascites fluid. Science 1983; 219:983-998.
2. Carmeliet P, Ferreira V, Breier G, Pollefeyt S, Kieckens L, Gertsenstein M, et al., Abnormal blood vessel development and lethality in embryos lacking a single VEGF allele. Nature 1996; 380:435-439.
3. Neufeld G, Cohen T, Gengrinovitch S, and Poltorak Z. Vascular endothelial growth factor (VEGF) and its receptors. FASEB J 1999; 13:9-22.
4. Hoeben A, Landuyt B, Highley M S, Wildiers H, Van Oosterom A T, De Bruijn E A. Vascular endothelial growth factor and angiogenesis. Pharmacol Rev 2004; 56(4):549-580. Review.
5. Baldwin M E, Stacker S A, and Achen M G. Molecular control of lymphangiogenesis. Bioessays 2002; 24:1030-1040.
6. Nagy J A, Vasile E, Feng D, Sundberg C, Brown L F, Detmar M J et al. Vascular permeability factor/vascular endothelial growth factor induces lymphangiogenesis as well as angiogenesis. J Exp Med 2002; 196:1497-1506.
7. Ohm J E, Gabrilovich D I, Sempowski G D, Kisseleva E, Parman K S, Nadaf S, et al. VEGF inhibits T-cell development and may contribute to tumor-induced immune suppression. Blood 2003; 101: 4878-4886.
8. Mann D R and Plant T M. Leptin and pubertal development. Semin Reprod Med 2002; 20:93-102.
9. Chaudhry I H, O'Donovan D G, Brenchley P E, Reid H, and Roberts I S. Vascular endothelial growth factor expression correlates with tumour grade and vascularity in gliomas. Histopathology 2001; 39:409-415.
10. Rubanyi G M. The future of human gene therapy. Mol Aspects Med 2001; 22(3):113-42. Review;
11. Kirsch M, Strasser J, Allende R, Bello L, Zhang J, and Black P M. Angiostatin suppresses malignant glioma growth in vivo. Cancer Res 1998; 58:4654-4659.
12. Lam P Y and Breakefield X O. Potential of gene therapy for brain tumors. Hum Mol Genet. 2001; 10:777-787.
13. Tanaka T, Cao Y, Folkman J, and Fine H A, Viral vector-targeted antiangiogenic gene therapy utilizing an angiostatin complementary DNA. Cancer Res 1998; 58:3362-3369.
14. Rubanyi G M, Editor, Angiogenesis in Health and Disease, Marcel Dekker, New York (2000), pp. 1-552.
15. Isner J M. Angiogenesis and collateral formation. In: K. L. March, Editor, Gene Transfer in the Cardiovascular System: Experimental Approaches and Therapeutic Implications, Kluwer Academic Publishers, Boston (1997), pp. 307-330.
16. Henry T D, Annex B H, Azrin M A, et al. Double blind, placebo controlled trial of recombinant human vascular endothelial growth factor: The VIVA Trial. J Am Coll Cardiol 1999; 33:384A.
17. Laham R J, Chronos N A, Leimbach M, et al., Results of Phase I open label dose escalation study of intracoronary and intravenous FGF-2 in patients with severe ischemic heart disease: 6 months follows-up. 3 μm Coll Cardiol 2000; 35 Suppl. A:73A.
18. Giordano F J, Ping P, McKirnan M D, et al., Intracoronary gene-transfer of fibroblast growth factor-5 increases blood flow and contractile function in an ischemic region of the heart. Nat Med 1996; 2:534-539.
19. Nabel E G and Nabel G J. Complex models for the study of gene function in cardiovascular biology. Annu Rev Physiol 1994; 56:741-761.
20. Yla-Herttuala S and Martin J F. Cardiovascular gene therapy. Lancet 2000; 355:213-222.
21. Springer M L, Chen A S, Kraft P E, Bednarski M, and. Blau H M. VEGF gene delivery to muscle: potential role for vasculogenesis in adults. Mol Cell 1998; 2:549-558.
22. Dormandy J A, Dole W P, and Rubanyi G M, Editors. Therapeutic Angiogenesis, Springer, Berlin (1999), pp. 1-184.
23. Sanghong B and March K L. Gene therapy for restenosis: Getting nearer the heart of the matter. Circ Res 1998; 82:295-305.
24. De Young M B and Dichek D A. Gene therapy for restenosis: Are we ready?. Circ Res 1998; 82:306-313.
25. Yaghmai R, Cutting G R. Optimized regulation of gene expression using artificial transcription factors. Mol Ther 2002; 5(6):685-94.
26. Tupler R, Perini G, and Green M R. Expressing the human genome. Nature 2001; 409:832-833.
27. Kang J S and Kim J S. Zinc finger proteins as designer transcription factors. J Biol Chem 2000; 275:8742-8748.
28. Liu P Q. Regulation of an endogenous locus using a panel of designed zinc finger proteins targeted to accessible chromatin regions. Activation of vascular endothelial growth factor A. J Biol Chem 2001; 276:11323-11334.
29. Zhang L. Synthetic zinc finger transcription factor action at an endogenous chromosomal site. Activation of the human erythropoietin gene. J Biol Chem 2000; 275: 33850-33860.
30. Beerli R R, Dreier B, and Barbas C F. Positive and negative regulation of endogenous genes by designed transcription factors. Proc Natl Acad Sci USA 2000; 97:1495-1500.
31. Dyson N and Harlow E. Adenovirus E1A targets key regulators of cell proliferation. Cancer Surv 1992; 12:161-195.
32. Whyte P, Ruley H E, Harlow E. Two regions of the adenovirus early region 1A proteins are required for transformation. J Virol 1988; 62:257-265.
33. Ptzera B M, Stiewea T, Parssanedjad K, Rega S, and Esche H. E1A is sufficient by itself to induce apoptosis independent of p53 and other adenoviral gene products. Cell death & Differentiation 2000; 7(2):177-188.
34. Bischoff J R, Kim D H, Williams A, Heise C, Horn S, Muna M, et al. An adenovirus mutant that replicates selectively in p53-deficient human tumor cells. Science 1996; 274:373-376.
35. Heise C, Sampson-Johannes A, Williams A, McCormick F, Von Hoff D D, and Kirn D H. ONYX-015, an E1B gene-attenuated adenovirus, causes tumor-specific cytolysis and antitumoral efficacy that can be augmented by standard chemotherapeutic agents. Nat Med 1997; 3:639-645.
36. Lee H, Kim J, Lee B, Chang J W, Ahn J, Park J O, et al. Oncolytic potential of E1B 55 kDa-deleted YKL-1 recombinant adenovirus: correlation with p53 functional status. Int J Cancer 2000; 88:454-463.
37. Kim J, Cho J Y, Kim J H, Jung K C, Yun C O. Evaluation of E1B gene-attenuated replicating adenoviruses for cancer gene therapy. Cancer Gene Ther 2002; 9:725-736.
38. Sauthoff H, Heitner S, Rom W N, Hay J G. Deletion of the adenoviral E1b-19 kD gene enhances tumor cell killing of a replicating adenoviral vector. Hum Gene Ther 2000; 11:379-388.
39. Nicosia R F and Ottinetti A. Modulation of microvascular growth and morphogenesis by reconstituted basement membrane gel in three-dimensional cultures of rat aorta: a comparative study of angiogenesis in Matrigel, collagen, fibrin, and plasma clot. In vitro Cell Dev Biol 1990; 26:119-128.
40. Zhou Z, Zhou R R, Guan H, Bucana C D, Kienerman E S. E1A gene therapy inhibits angiogenesis in a Ewing's sarcoma animal model. Mol Cancer Ther 2003; 2(12): 1313-1319.
41. Snowden A W, Zhang L, Urnov F, Dent C, Jouvenot Y, Zhong X, et al. Repression of vascular endothelial growth factor A in glioblastoma cells using engineered zinc finger transcription factors. Cancer Res 2003; 63(24):8968-8976.
42. Liu P Q, Rebar E J, Zhang L, Liu Q, Jamieson A C, Liang Y, et al. Regulation of an endogenous locus using a panel of designed zinc finger proteins targeted to accessible chromatin regions. Activation of vascular endothelial growth factor A. J Biol Chem 2001; 276:11323-11334.
43. Rebar E J, Huang Y, Hickey R, Nath A K, Meoli D, Nath S, et al. Induction of angiogenesis in a mouse model using engineered transcription factors. Nat Med 2002; 8(12): 1427-1432. Epub 2002 Nov. 4.
44. Bae K H, Kwon Y D, Shin H C, Hwang M S, Ryu E H, Park K S, et al. Human zinc fingers as building blocks in the construction of artificial transcription factors. Nat Biotechnol 2003; 21(3):275-280. Epub 2003 Feb. 18.
45. Cheng S Y, Huang H J, Nagane M, Ji X D, Wang D, Shih C C, et al. Suppression of glioblastoma angiogenicity and tumorigenicity by inhibition of endogenous expression of vascular endothelial growth factor. Proc Natl Acad Sci USA 1996; 93:8502-8507.
46. Grunstein J, Masbad A, Hickey R, Giordano F J, and Johnson R S. Isoforms of vascular endothelial growth factor act in a coordinate fashion to recruit and expand tumor vasculature. Mol Cell Biol 2000; 20:7282-7291.
47. Dvorak H F. Angiogenesis: update 2005. J Thromb Haemost 2005; 3(8):1835-1842.
48. Whitlock P R, Hackett N R, Leopold P L, Rosengart T K, Crystal R G. Adenovirus-mediated transfer of a minigene expressing multiple isoforms of VEGF is more effective at inducing angiogenesis than comparable vectors expressing individual VEGF cDNAs. Mol Ther 2004; 9(1):67-75.

What is claimed is:

1. A recombinant adenovirus capable of regulating angiogenesis, comprising: (a) an adenoviral ITR (inverted terminal repeat) nucleotide sequence; and (b) a nucleotide sequence for regulating transcription of a VEGF-A (vascular endothelial growth factor-A) gene comprising (i) a nucleotide sequence encoding a DNA binding domain comprising a zinc finger domain to bind to a site in a VEGF-A promoter sequence as set forth in nucleotides 1-2362 of SEQ ID NO:1, wherein the nucleotide sequence encoding the DNA binding domain codes for the amino acid sequence of SEQ ID NO:2, and (ii) a nucleotide sequence encoding a KOX domain linked to the nucleotide sequence encoding the DNA binding domain; wherein the recombinant adenovirus comprises a deleted E3 region and the nucleotide sequence for regulating transcription of a VEGF-A gene is inserted into the deleted E3 region; wherein the recombinant adenovirus comprises an inactivated E1B 19/E1B 55 gene; and wherein the recombinant adenovirus comprises a mutated active E1A gene having a mutated Rb (retinoblastoma protein) binding region.

2. A method for treating brain cancer, lung cancer, liver cancer, or cervical cancer which comprises administering to a patient a pharmaceutical composition comprising a therapeutically effective amount of the recombinant adenovirus of claim 1; and a pharmaceutically acceptable carrier.

3. The method according to claim 2, wherein the recombinant adenovirus comprises a nucleotide sequence encoding a KOX domain in the nucleotide sequence for regulating transcription of the VEGF-A gene.

* * * * *

SEQUENCE LISTING

```
<160> NUMBER OF SEQ ID NOS: 34

<210> SEQ ID NO 1
<211> LENGTH: 3480
<212> TYPE: DNA
<213> ORGANISM: Homo sapiens
<220> FEATURE:
<221> NAME/KEY: misc_RNA
<222> LOCATION: (2363)
<223> OTHER INFORMATION: mRNA start site

<400> SEQUENCE: 1
gaattctgtg ccctcactcc cctggatccc tgggcaaagc cccagaggga aacacaaaca      60
ggttgttgta acacaccttg ctgggtacca ccatggagga cagttggctt atggggtgg     120 ggggtgcctg gggccacgga gtgactggtg atggctatcc ctccttggaa ccctccagc     180 ctcctcttag cttcagattt gtttatttgt tttttactaa gacctgctct ttcaggtctg     240
ttggctcttt tagggctga agaaggccga gttgagaagg gatgcaaggg aggggccag      300
```

```
aatgagccct tagggctcag agcctccatc ctgccccaag atgtctacag cttgtgctcc    360
tggggtgcta gaggcgcaca aggaggaaag ttagtggctt cccttccata tcccgttcat    420
cagcctagag catggagccc aggtgaggag gcctgcctgg agggggccc  tgagccagga    480 aataaacatt tactaactgt acaaagacct tgtccctgct gctggggagc ctgccaagtg    540
gtggagacag gactagtgca cgaatgatgg aaagggaggg ttggggtggg tgggagccag    600 ccctttcct  cataagggcc ttaggacacc ataccgatgg aactgggggt actggggagg    660
taacctagca cctccaccaa accacagcaa catgtgctga ggatggggct gactaggtaa    720
gctccctgga gcgttttggt taaattgagg gaaattgctg cattcccatt ctcagtccat    780
gcctccacag aggctatgcc agctgtaggc cagaccctgg caagatctgg gtggataatc    840
agactgactg gcctcagagc cccaactttg ttccctgggg cagcctggaa atagccaggt    900
cagaaaccag ccaggaattt ttccaagctg cttcctatat gcaagaatgg gatgggggcc    960
tttgggagca cttagggaag atgtggagag ttggaggaaa aggggcttg  gaggtaaggg   1020 aggggactgg gggaaggata ggggagaagc tgtgagcctg gagaagtagc caagggatcc   1080
tgagggaatg ggggagctga gacgaaaccc ccatttctat tcagaagatg agctatgagt   1140
ctgggcttgg gctgatagaa gccttggccc ctggcctggt gggagctctg ggcagctggc   1200
ctacagacgt tccttagtgc tggcgggtag gtttgaatca tcacgcaggc cctggcctcc   1260
acccgccccc accagccccc tggcctcagt tccctggcaa catctggggt tgggggggca   1320
gcaggaacaa gggcctctgt ctgcccagct gcctccccct ttgggttttg ccagactcca   1380
cagtgcatac gtgggctcca acaggtcctc ttccctccca gtcactgact aaccccggaa   1440
ccacacagct tccgttctc  agctccacaa acttggtgcc aaattcttct cccctgggaa   1500
gcatccctgg acacttccca aaggaccca  gtcactccag cctgttggct gccgctcact   1560
ttgatgtctg caggccagat gagggctcca gatggcacat tgtcagaggg acacactgtg   1620 gccctgtgc  ccagccctgg gctctctgta catgaagcaa ctccagtccc aaatatgtag   1680
ctgtttggga ggtcagaaat aggggtcca  ggagcaaact ccccccaccc cctttccaaa   1740
gcccattccc tctttagcca gagccggggt gtgcagacgg cagtcactag ggggcgctcg   1800
gccaccacag ggaagctggg tgaatggagc gagcagcgtc ttcgagagtg aggacgtgtg   1860
tgtctgtgtg ggtgagtgag tgtgtgcgtg tggggttgag ggtgttggag cggggagaag   1920 gccagggggtc actccaggat ccaacagat  ctgtgtgtcc ctctccccac ccgtccctgt   1980
ccggctctcc gccttcccct gcccccttca atattcctag caaagaggga acggctctca   2040
ggccctgtcc gcacgtaacc tcactttcct gctccctcct cgccaatgcc ccgcgggcgc   2100
gtgtctctgg acagagtttc cggggcgga  tgggtaattt tcaggctgtg aaccttggtg   2160
ggggtcgagc ttccccttca ttgcggcggg ctgcgggcca ggcttcactg ggcgtccgca   2220
gagcccgggc ccgagccgcg tgtggagggg ctgaggctcg cctgtccccg ccccccgggg   2280
cgggccgggg gcgggtccc  ggcggggcgg agccatgcgc ccccccttt  ttttttaaa    2340 agtcggctgg tagcggggag gatcgcggag gcttgggggca gccgggtagc tcggaggtcg   2400
tggcgctggg ggctagcacc agcgctctgt cggaggcgc  agcggttagg tggaccggtc   2460
agcggactca ccggccaggg cgctcggtgc tggaatttga tattcattga tccgggtttt   2520
atccctcttc ttttttctta aacattttt  tttaaaactg tattgtttct cgttttaatt   2580 tattttttgct tgccattccc cacttgaatc gggccgacgg cttggggaga ttgctctact   2640 tcccaaatc  actgtggatt ttggaaacca gcagaaagag gaaagaggta gcaagagctc   2700
```

```
cagagagaag tcgaggaaga gagagacggg gtcagagaga gcgcgcgggc gtgcgagcag    2760
cgaaagcgac aggggcaaag tgagtgacct gcttttgggg gtgaccgccg gagcgcggcg    2820
tgagccctcc cccttgggat cccgcagctg accagtcgcg ctgacggaca gacagacaga    2880
caccgccccc agccccagct accacctcct ccccggccgg cggcggacag tggacgcggc    2940
ggcgagccgc gggcaggggc cggagcccgc gcccggaggc ggggtggagg gggtcggggc    3000
tcgcggcgtc gcactgaaac ttttcgtcca acttctgggc tgttctcgct tcggaggagc    3060
cgtggtccgc gcggggaag ccgagccgag cggagccgcg agaagtgcta gctcgggccg     3120
ggaggagccg cagccggagg aggggagga ggaagaagag aaggaagagg agaggggcc      3180 gcagtggcga ctcggcgctc ggaagccggg ctcatggacg ggtgaggcgg cggtgtgcgc    3240
agacagtgct ccagccgcgc gcgctcccca ggccctggcc cgggcctcgg gccggggagg    3300
aagagtagct cgccgaggcg ccgaggagag cgggccgccc cacagcccga gccggagagg    3360
gagcgcgagc cgccgccggcc ccggtcgggc tccgaaaacc atgaactttc tgctgtcttg   3420
ggtgcattgg agccttgcct tgctgctcta cctccaccat gccaaggtaa gcggtcgtgc    3480
```

```
<210> SEQ ID NO 2
<211> LENGTH: 83
<212> TYPE: PRT
<213> ORGANISM: Artificial Sequence
<220> FEATURE:
<223> OTHER INFORMATION: completely synthesized zinc finger protein

<400> SEQUENCE: 2

Tyr Lys Cys Gly Gln Cys Gly Lys Phe Tyr Ser Gln Val Ser His Leu
  1               5                  10                  15

Thr Arg His Gln Lys Ile His Thr Gly Glu Lys Pro Phe Gln Cys Lys
             20                  25                  30

Thr Cys Gln Arg Lys Phe Ser Arg Ser Asp His Leu Lys Thr His Thr
         35                  40                  45

Arg Thr His Thr Gly Glu Lys Pro Tyr Lys Cys Met Glu Cys Gly Lys
     50                  55                  60

Ala Phe Asn Arg Arg Ser His Leu Thr Arg His Gln Arg Ile His Thr
 65                  70                  75                  80

Gly Glu Lys
```

```
<210> SEQ ID NO 3
<211> LENGTH: 83
<212> TYPE: PRT
<213> ORGANISM: Artificial Sequence
<220> FEATURE:
<223> OTHER INFORMATION: completely synthesized zinc finger protein

<400> SEQUENCE: 3

Tyr Lys Cys Gly Gln Cys Gly Lys Phe Tyr Ser Gln Val Ser His Leu
  1               5                  10                  15

Thr Arg His Gln Lys Ile His Thr Gly Glu Lys Pro Phe Gln Cys Lys
             20                  25                  30

Thr Cys Gln Arg Lys Phe Ser Arg Ser Asp His Leu Lys Thr His Thr
         35                  40                  45

Arg Thr His Thr Gly Glu Lys Pro Tyr Ile Cys Arg Lys Cys Gly Arg
     50                  55                  60

Gly Phe Ser Arg Lys Ser Asn Leu Ile Arg His Gln Arg Thr His Thr
 65                  70                  75                  80
```

Gly Glu Lys

<210> SEQ ID NO 4
<211> LENGTH: 83
<212> TYPE: PRT
<213> ORGANISM: Artificial Sequence
<220> FEATURE:
<223> OTHER INFORMATION: completely synthesized zinc finger protein

<400> SEQUENCE: 4

Tyr Lys Cys Met Glu Cys Gly Lys Ala Phe Asn Arg Arg Ser His Leu
1               5                   10                  15

Thr Arg His Gln Arg Ile His Thr Gly Glu Lys Pro Phe Gln Cys Lys
            20                  25                  30

Thr Cys Gln Arg Lys Phe Ser Arg Ser Asp His Leu Lys Thr His Thr
        35                  40                  45

Arg Thr His Thr Gly Glu Lys Pro Tyr Lys Cys Met Glu Cys Gly Lys
    50                  55                  60

Ala Phe Asn Arg Arg Ser His Leu Thr Arg His Gln Arg Ile His Thr
65                  70                  75                  80

Gly Glu Lys

<210> SEQ ID NO 5
<211> LENGTH: 111
<212> TYPE: PRT
<213> ORGANISM: Artificial Sequence
<220> FEATURE:
<223> OTHER INFORMATION: completely synthesized zinc finger protein

<400> SEQUENCE: 5

Tyr Lys Cys Glu Glu Cys Gly Lys Ala Phe Arg Gln Ser Ser His Leu
1               5                   10                  15

Thr Thr His Lys Ile Ile His Thr Gly Glu Lys Pro Tyr Ser Cys Gly
            20                  25                  30

Ile Cys Gly Lys Ser Phe Ser Asp Ser Ser Ala Lys Arg Arg His Cys
        35                  40                  45

Ile Leu His Thr Gly Glu Lys Pro Tyr Ile Cys Arg Lys Cys Gly Arg
    50                  55                  60

Gly Phe Ser Arg Lys Ser Asn Leu Ile Arg His Gln Arg Thr His Thr
65                  70                  75                  80

Gly Glu Lys Pro Phe Gln Cys Lys Thr Cys Gln Arg Lys Phe Ser Arg
            85                  90                  95

Ser Asp His Leu Lys Thr His Thr Arg Thr His Thr Gly Glu Lys
        100                 105                 110

<210> SEQ ID NO 6
<211> LENGTH: 260
<212> TYPE: PRT
<213> ORGANISM: Homo sapiens

<400> SEQUENCE: 6

Tyr Leu Pro Asp Thr Asp Asp Arg His Arg Ile Glu Glu Lys Arg Lys
1               5                   10                  15

Arg Thr Tyr Glu Thr Phe Lys Ser Ile Met Lys Lys Ser Pro Phe Ser
            20                  25                  30

Gly Pro Thr Asp Pro Arg Pro Pro Arg Arg Ile Ala Val Pro Ser
        35                  40                  45

Arg Ser Ser Ala Ser Val Pro Lys Pro Ala Pro Gln Pro Tyr Pro Phe
    50                  55                  60

```
Thr Ser Ser Leu Ser Thr Ile Asn Tyr Asp Glu Phe Pro Thr Met Val
 65                  70                  75                  80

Phe Pro Ser Gly Gln Ile Ser Gln Ala Ser Ala Leu Ala Pro Ala Pro
                 85                  90                  95

Pro Gln Val Leu Pro Gln Ala Pro Ala Pro Ala Pro Ala Pro Ala Met
            100                 105                 110

Val Ser Ala Leu Ala Gln Ala Pro Ala Pro Val Pro Val Leu Ala Pro
            115                 120                 125

Gly Pro Pro Gln Ala Val Ala Pro Pro Ala Pro Lys Pro Thr Gln Ala
130                 135                 140

Gly Glu Gly Thr Leu Ser Glu Ala Leu Leu Gln Leu Gln Phe Asp Asp
145                 150                 155                 160

Glu Asp Leu Gly Ala Leu Leu Gly Asn Ser Thr Asp Pro Ala Val Phe
                165                 170                 175

Thr Asp Leu Ala Ser Val Asp Asn Ser Glu Phe Gln Gln Leu Leu Asn
            180                 185                 190

Gln Gly Ile Pro Val Ala Pro His Thr Thr Glu Pro Met Leu Met Glu
            195                 200                 205

Tyr Pro Glu Ala Ile Thr Arg Leu Val Thr Ala Gln Arg Pro Pro Asp
210                 215                 220

Pro Ala Pro Ala Pro Leu Gly Ala Pro Gly Leu Pro Asn Gly Leu Leu
225                 230                 235                 240

Ser Gly Asp Glu Asp Phe Ser Ser Ile Ala Asp Met Asp Phe Ser Ala
                245                 250                 255

Leu Leu Ser Gln
            260

<210> SEQ ID NO 7
<211> LENGTH: 96
<212> TYPE: PRT
<213> ORGANISM: Homo sapiens

<400> SEQUENCE: 7

Asp Ala Lys Ser Leu Thr Ala Trp Ser Arg Thr Leu Val Thr Phe Lys
 1               5                  10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45

Leu Val Ser Leu Gly Tyr Gln Leu Thr Lys Pro Asp Val Ile Leu Arg
 50                  55                  60

Leu Glu Lys Gly Glu Glu Pro Trp Leu Val Glu Arg Glu Ile His Gln
 65                  70                  75                  80

Glu Thr His Pro Asp Ser Glu Thr Ala Phe Glu Ile Lys Ser Ser Val
                85                  90                  95

<210> SEQ ID NO 8
<211> LENGTH: 249
<212> TYPE: DNA
<213> ORGANISM: Artificial Sequence
<220> FEATURE:
<223> OTHER INFORMATION: nucleotide sequence encoding completely
      synthesized zinc finger protein

<400> SEQUENCE: 8
tataaatgcg gccagtgtgg gaagttctac tcgcaggtct cccacctcac ccgccaccag    60
```

```
aaaatccaca ccggggaaaa accgttccag tgtaaaactt gtcagcgaaa gttctcccgg    120
tccgaccacc tgaagaccca caccaggact cataccgggg aaaaaccgta taagtgcatg    180
gagtgtggga aggcttttaa ccgcaggtca cacctcacac ggcaccagcg gattcacacc    240
ggtgaaaaa                                                            249
```

```
<210> SEQ ID NO 9
<211> LENGTH: 780
<212> TYPE: DNA
<213> ORGANISM: Homo sapiens

<400> SEQUENCE: 9
tacctgccag atacagacga tcgtcaccgg attgaggaga acgtaaaag gacatatgag     60 accttcaaga gcatcatgaa gaagagtcct ttcagcggac ccaccgaccc ccggcctcca    120
cctcgacgca ttgctgtgcc ttcccgcagc tcagcttctg tccccaagcc agcacccccag  180 ccctatccct ttacgtcatc cctgagcacc atcaactatg atgagtttcc caccatggtg    240
tttccttctg ggcagatcag ccaggcctcg gccttggccc cggcccctcc caagtcctg     300 ccccaggctc cagccctgc ccctgctcca gccatggtat cagctctggc ccaggcccca    360
gcccctgtcc cagtcctagc cccaggccct cctcaggctg tggccccacc tgcccccaag    420
cccacccagg ctggggaagg aacgctgtca gaggccctgc tgcagctgca gtttgatgat    480
gaagacctgg gggccttgct tggcaacagc acagacccag ctgtgttcac agacctggca    540
tccgtcgaca actccgagtt tcagcagctg ctgaaccagg catacctgt ggccccccac     600 acaactgagc ccatgctgat ggagtaccct gaggctataa ctcgcctagt gacaggggag    660
aggccccccg acccagctcc tgctccactg ggggctccgg ggctccccaa tggcctcctt    720
tcaggagatg aagacttctc ctccattgcg gacatggact tctcagccct gctgagtcag    780
```

```
<210> SEQ ID NO 10
<211> LENGTH: 288
<212> TYPE: DNA
<213> ORGANISM: Homo sapiens

<400> SEQUENCE: 10
gatgctaagt cactaactgc ctggtcccgg acactggtga ccttcaagga tgtatttgtg     60
gacttcacca gggaggagtg gaagctgctg gacactgctc agcagatcgt gtacagaaat    120
gtgatgctgg agaactataa gaacctggtt tccttgggtt atcagcttac taagccagat    180
gtgatcctcc ggttggagaa gggagaagag ccctggctgg tggagagaga aattcaccaa    240
gagacccatc ctgattcaga gactgcattt gaaatcaaat catcagtt                 288
```

```
<210> SEQ ID NO 11
<211> LENGTH: 249
<212> TYPE: DNA
<213> ORGANISM: Artificial Sequence
<220> FEATURE:
<223> OTHER INFORMATION: nucleotide sequence encoding completely
      synthesized zinc finger protein

<400> SEQUENCE: 11
tatgagtgtc acgattgcgg aaagtccttt aggcagagca cccacctcac tcggcaccgg     60
agaatccaca ccggggaaaa accgttccag tgtaaaactt gtcagcgaaa gttctcccgg    120
tccgaccacc tgaagaccca caccaggact cataccgggg aaaaaccgta taagtgcatg    180
gagtgtggga aggcttttaa ccgcaggtca cacctcacac ggcaccagcg gattcacacc    240
```

```
                                                                    -continued
ggtgaaaaa                                                                  249

<210> SEQ ID NO 12
<211> LENGTH: 83
<212> TYPE: PRT
<213> ORGANISM: Artificial Sequence
<220> FEATURE:
<223> OTHER INFORMATION: completely synthesized zinc finger protein

<400> SEQUENCE: 12

Tyr Glu Cys His Asp Cys Gly Lys Ser Phe Arg Gln Ser Thr His Leu
 1               5                  10                  15

Thr Arg His Arg Arg Ile His Thr Gly Glu Lys Pro Phe Gln Cys Lys
            20                  25                  30

Thr Cys Gln Arg Lys Phe Ser Arg Ser Asp His Leu Lys Thr His Thr
        35                  40                  45

Arg Thr His Thr Gly Glu Lys Pro Tyr Lys Cys Met Glu Cys Gly Lys
    50                  55                  60

Ala Phe Asn Arg Arg Ser His Leu Thr Arg His Gln Arg Ile His Thr
65                  70                  75                  80

Gly Glu Lys

<210> SEQ ID NO 13
<211> LENGTH: 23
<212> TYPE: PRT
<213> ORGANISM: Homo sapiens

<400> SEQUENCE: 13

Tyr Lys Cys Lys Gln Cys Gly Lys Ala Phe Gly Cys Pro Ser Asn Leu
 1               5                  10                  15

Arg Arg His Gly Arg Thr His
            20

<210> SEQ ID NO 14
<211> LENGTH: 23
<212> TYPE: PRT
<213> ORGANISM: Homo sapiens

<400> SEQUENCE: 14

Tyr Ser Cys Gly Ile Cys Gly Lys Ser Phe Ser Asp Ser Ser Ala Lys
 1               5                  10                  15

Arg Arg His Cys Ile Leu His
            20

<210> SEQ ID NO 15
<211> LENGTH: 23
<212> TYPE: PRT
<213> ORGANISM: Homo sapiens

<400> SEQUENCE: 15

Tyr Thr Cys Ser Asp Cys Gly Lys Ala Phe Arg Asp Lys Ser Cys Leu
 1               5                  10                  15

Asn Arg His Arg Arg Thr His
            20

<210> SEQ ID NO 16
<211> LENGTH: 23
<212> TYPE: PRT
<213> ORGANISM: Homo sapiens

<400> SEQUENCE: 16
```

```
Tyr Lys Cys Gly Gln Cys Gly Lys Phe Tyr Ser Gln Val Ser His Leu
 1               5                  10                  15

Thr Arg His Gln Lys Ile His
            20
```

<210> SEQ ID NO 17
<211> LENGTH: 23
<212> TYPE: PRT
<213> ORGANISM: Homo sapiens

<400> SEQUENCE: 17

```
Tyr Lys Cys Glu Glu Cys Gly Lys Ala Phe Arg Gln Ser Ser His Leu
 1               5                  10                  15

Thr Thr His Lys Ile Ile His
            20
```

<210> SEQ ID NO 18
<211> LENGTH: 23
<212> TYPE: PRT
<213> ORGANISM: Homo sapiens

<400> SEQUENCE: 18

```
Tyr Glu Cys Glu Lys Cys Gly Lys Ala Phe Asn Gln Ser Ser Asn Leu
 1               5                  10                  15

Thr Arg His Lys Lys Ser His
            20
```

<210> SEQ ID NO 19
<211> LENGTH: 23
<212> TYPE: PRT
<213> ORGANISM: Homo sapiens

<400> SEQUENCE: 19

```
Tyr Val Cys Ser Lys Cys Gly Lys Ala Phe Thr Gln Ser Ser Asn Leu
 1               5                  10                  15

Thr Val His Gln Lys Ile His
            20
```

<210> SEQ ID NO 20
<211> LENGTH: 23
<212> TYPE: PRT
<213> ORGANISM: Homo sapiens

<400> SEQUENCE: 20

```
Tyr Lys Cys Pro Asp Cys Gly Lys Ser Phe Ser Gln Ser Ser Ser Leu
 1               5                  10                  15

Ile Arg His Gln Arg Thr His
            20
```

<210> SEQ ID NO 21
<211> LENGTH: 25
<212> TYPE: PRT
<213> ORGANISM: Homo sapiens

<400> SEQUENCE: 21

```
Tyr Val Cys Asp Val Glu Gly Cys Thr Trp Lys Phe Ala Arg Ser Asp
 1               5                  10                  15

Glu Leu Asn Arg His Lys Lys Arg His
            20                  25
```

<210> SEQ ID NO 22
<211> LENGTH: 23

<212> TYPE: PRT
<213> ORGANISM: Homo sapiens

<400> SEQUENCE: 22

Phe Gln Cys Lys Thr Cys Gln Arg Lys Phe Ser Arg Ser Asp His Leu
 1               5                  10                  15

Lys Thr His Thr Arg Thr His
            20

<210> SEQ ID NO 23
<211> LENGTH: 23
<212> TYPE: PRT
<213> ORGANISM: Homo sapiens

<400> SEQUENCE: 23

Tyr Lys Cys Met Glu Cys Gly Lys Ala Phe Asn Arg Arg Ser His Leu
 1               5                  10                  15

Thr Arg His Gln Arg Ile His
            20

<210> SEQ ID NO 24
<211> LENGTH: 23
<212> TYPE: PRT
<213> ORGANISM: Homo sapiens

<400> SEQUENCE: 24

Tyr Ile Cys Arg Lys Cys Gly Arg Gly Phe Ser Arg Lys Ser Asn Leu
 1               5                  10                  15

Ile Arg His Gln Arg Thr His
            20

<210> SEQ ID NO 25
<211> LENGTH: 23
<212> TYPE: PRT
<213> ORGANISM: Homo sapiens

<400> SEQUENCE: 25

Tyr Glu Cys Asp His Cys Gly Lys Ala Phe Ser Val Ser Ser Asn Leu
 1               5                  10                  15

Asn Val His Arg Arg Ile His
            20

<210> SEQ ID NO 26
<211> LENGTH: 23
<212> TYPE: PRT
<213> ORGANISM: Homo sapiens

<400> SEQUENCE: 26

Tyr Thr Cys Lys Gln Cys Gly Lys Ala Phe Ser Val Ser Ser Ser Leu
 1               5                  10                  15

Arg Arg His Glu Thr Thr His
            20

<210> SEQ ID NO 27
<211> LENGTH: 23
<212> TYPE: PRT
<213> ORGANISM: Homo sapiens

<400> SEQUENCE: 27

Tyr Glu Cys Asn Tyr Cys Gly Lys Thr Phe Ser Val Ser Ser Thr Leu
 1               5                  10                  15

Ile Arg His Gln Arg Ile His
            20

<210> SEQ ID NO 28
<211> LENGTH: 23
<212> TYPE: PRT
<213> ORGANISM: Homo sapiens

<400> SEQUENCE: 28

Tyr Arg Cys Glu Glu Cys Gly Lys Ala Phe Arg Trp Pro Ser Asn Leu
1               5                   10                  15

Thr Arg His Lys Arg Ile His
            20

<210> SEQ ID NO 29
<211> LENGTH: 23
<212> TYPE: PRT
<213> ORGANISM: Homo sapiens

<400> SEQUENCE: 29

Tyr Glu Cys Asp His Cys Gly Lys Ser Phe Ser Gln Ser Ser His Leu
1               5                   10                  15

Asn Val His Lys Arg Thr His
            20

<210> SEQ ID NO 30
<211> LENGTH: 23
<212> TYPE: PRT
<213> ORGANISM: Homo sapiens

<400> SEQUENCE: 30

Phe Leu Cys Gln Tyr Cys Ala Gln Arg Phe Gly Arg Lys Asp His Leu
1               5                   10                  15

Thr Arg His Met Lys Lys Ser
            20

<210> SEQ ID NO 31
<211> LENGTH: 24
<212> TYPE: PRT
<213> ORGANISM: Artificial Sequence
<220> FEATURE:
<223> OTHER INFORMATION: completely synthesized zinc finger domain

<400> SEQUENCE: 31

Tyr Arg Cys Lys Tyr Cys Asp Arg Ser Phe Ser Asp Ser Ser Asn Leu
1               5                   10                  15

Gln Arg His Val Arg Asn Ile His
            20

<210> SEQ ID NO 32
<211> LENGTH: 23
<212> TYPE: PRT
<213> ORGANISM: Homo sapiens

<400> SEQUENCE: 32

Tyr Glu Cys His Asp Cys Gly Lys Ser Phe Arg Gln Ser Thr His Leu
1               5                   10                  15

Thr Arg His Arg Arg Ile His
            20

<210> SEQ ID NO 33
<211> LENGTH: 902

```
<212> TYPE: DNA
<213> ORGANISM: Artificial Sequence
<220> FEATURE:
<223> OTHER INFORMATION: m-hTERT

<400> SEQUENCE: 33
agatctctcc gctggggccc tcgctggcgt ccctgcaccc tgggagcgcg agcggcgcgc    60
gggcggggaa gcgcggccca gaccccgggg tccgcccgga gcagctgcgc tgtcggggcc   120
aggccgggct cccagtggat tcgcgggcac agacgcccag gaccgcgctt cccacgtggc   180
ggagggactg gggacccggg caccgtcct gccccttcac cttccagctc cgcctcctcc    240
gcgcggaccc cgccccgtcc cgaccctcc cgggtcccg gccagcccc ctccgggccc      300 tcccagcccc tccccttcct ttccgcggcc ccgccctctc ctcgcggcgc gagtttcagg   360
cagcgctgcg tcctgctgcg cacgtgggaa gccctggccc cggccacccc cgcgtgaagc   420
ttgcatgcct gcaggtcgac tctagaggat ctactagtca tatggatgag ctcgagctgc   480
accctgggag cgcgagcggc gcgcgggcgg ggaagcgcgg cccagacccc cgggtccgcc   540
cggagcagct gcgctgtcgg ggccaggccg ggctcccagt ggattcgcgg gcacagacgc   600
ccaggaccgc gcttcccacg tggcggaggg actggggacc cgggcacccg tcctgccct   660 tcaccttcca gctccgcctc ctccgcgcgg accccgcccc gtcccgaccc ctcccgggtc   720
cccggcccag ccccctccgg gccctcccag ccctcccct tcctttccgc ggccccgccc   780
tctcctcgag ctcgagatcg gatccccggg taccgaggcg aattcggctt ctcgagccac   840
tcttgagtgc cagcgagtag agttttctcc tccgagccgc tccgacaccg ggactgaaaa   900
tg                                                                  902

<210> SEQ ID NO 34
<211> LENGTH: 263
<212> TYPE: DNA
<213> ORGANISM: Homo sapiens

<400> SEQUENCE: 34
caaagcctgc gcgcgccccg ccccgccatt ggccgtaccg ccccgcgccg ccgccccatc    60
tcgcccctcg ccgccgggtc cgggcgcgtt aaagccaata ggaacccgcc gccgttgttc   120
ccgtcacggc cggggcagcc aattgtgcgg gcgctcggcg gctcgtggct ctttcgcggc   180
aaaaaggatt tgggcgcgta aaagtggccc gggactttgc aggcagcggc ggcccggggg   240
gcggagcggg gatcgagccc tcg                                          263
```